United States Patent
Gokce et al.

(10) Patent No.: US 7,348,408 B2
(45) Date of Patent: Mar. 25, 2008

(54) FUSION PROTEINS

(75) Inventors: Isa Gokce, Tokat (TR); Gregor Anderluh, Ljubljana (SI); Jeremy Hugh Lakey, Newcastle upon Tyne (GB)

(73) Assignee: Newcastle University Ventures Limited, Newcastle Upon Tyne (GB)

( * ) Notice: Subject to any disclaimer, the term of this patent is extended or adjusted under 35 U.S.C. 154(b) by 0 days.

(21) Appl. No.: 10/501,071

(22) PCT Filed: Jan. 10, 2003

(86) PCT No.: PCT/GB03/00078

§ 371 (c)(1),
(2), (4) Date: Feb. 14, 2005

(87) PCT Pub. No.: WO03/057708

PCT Pub. Date: Jul. 17, 2003

(65) Prior Publication Data

US 2005/0130269 A1    Jun. 16, 2005

(30) Foreign Application Priority Data

Jan. 10, 2002   (GB) ................................. 0200689.8

(51) Int. Cl.
*C07K 14/00* (2006.01)
(52) U.S. Cl. ..................................... 530/350
(58) Field of Classification Search ............... 530/350; 437/69.1; 435/7.1; 514/12

See application file for complete search history.

(56) References Cited

U.S. PATENT DOCUMENTS 5,087,564 A * 2/1992 Mai et al. .................. 435/69.7
2002/0137049 A1* 9/2002 Mark et al. .................... 435/6

FOREIGN PATENT DOCUMENTS

EP          0299810 A1    1/1989
WO       WO01/21817       3/2001

OTHER PUBLICATIONS

Riechmann et al, CELL, vol. 90, pp. 351-360, Jul. 25, 1997, The C-Terminal Domain of TolA is the Coreceptor for Filamentous . . . .
Lubkowski et al, STRUCTURE, vol. 7, No. 6, 1999, pp. 711-722, Filamentous phage infection: crystal structure of g3p in . . . .
Derouiche et al, BIOLOGY 143, 1997, pp. 3185-3192, Binding of Colicins A and E1 to purified TolA domains.

(Continued)

*Primary Examiner*—Robert B. Mondesi
(74) *Attorney, Agent, or Firm*—Jacobson Holman PLLC

(57) ABSTRACT

The present invention relates to fusion proteins (fusion polypeptides), particularly for use in expression and/or purification systems. The present inventors have found that the TolAIII domain has remarkable properties which are of particular use as a fusion protein partner to achieve high levels of expression in a host cell. In one aspect of the invention, a TolAIII domain or a functional homologue, fragment, or derivative thereof is located towards the N-terminus of the fusion polypeptide and a non-TolA polypeptide is located towards the C-terminus of the fusion polypeptide.

17 Claims, 9 Drawing Sheets

OTHER PUBLICATIONS

Figure 1:
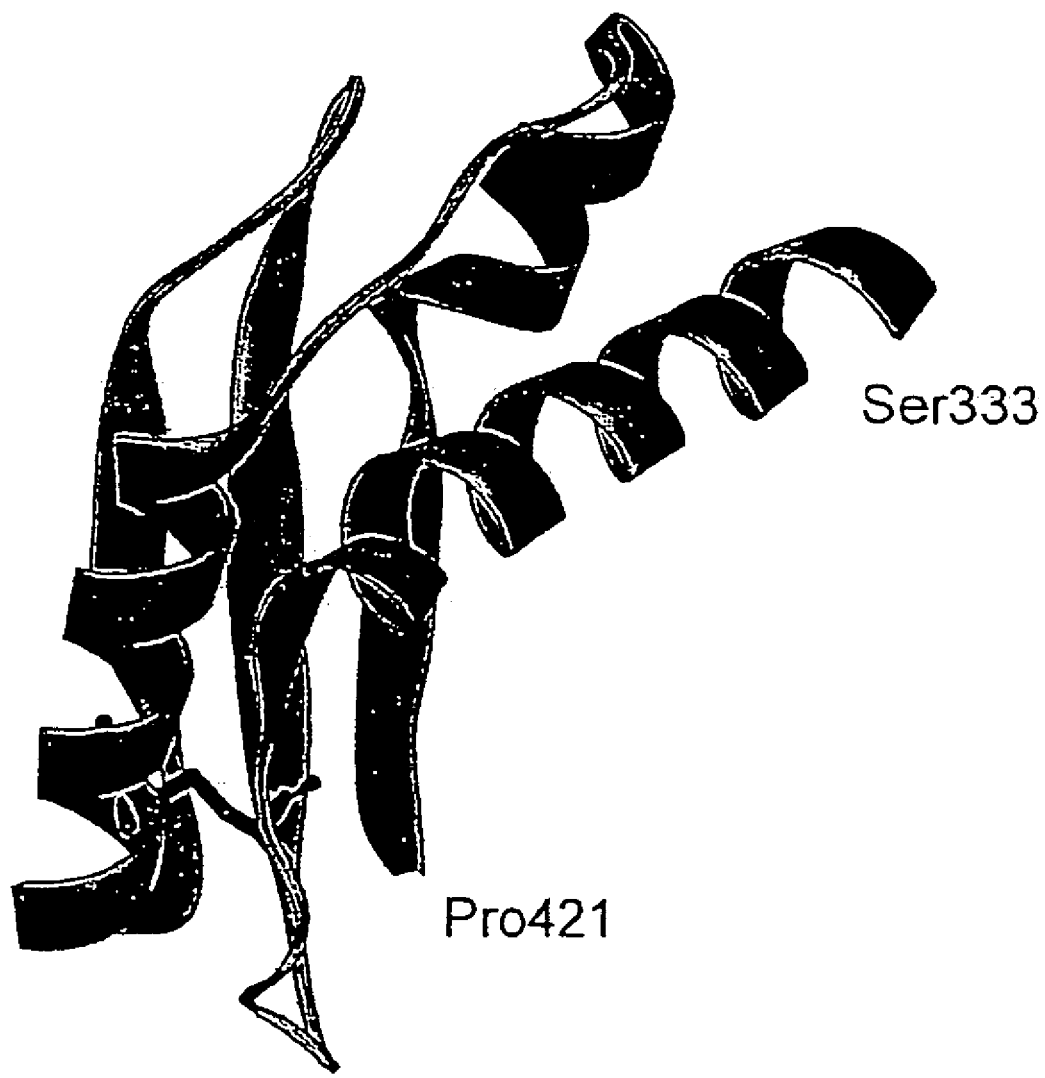

Wan et al, Protein Expression & Purification 14, pp. 13-22, 1998, TolAIII Co-overexpression Facilitates the Recovery of . . . .

LaVallie et al, Bio/Technology, vol. 11, pp. 187-193, Feb. 11, 1993, A Thioredoxin Gene Fusion Expression System that . . . .

Deprez et al, Biochemistry 41, 2002, pp. 2589-2598, Macromolecular Import into *Escherichia coli*: The TolA C-Terminal . . . .

Walburger et al, Molecular Microbiology 44 (3), pp. 695-708, 2002, The Tol/Pal system function requires an interaction . . . .

Anderluh et al, Protein Expression & Purification 28, pp. 173-181, 2003, Expression of proteins using the third domain of . . . .

Gokce et al, J Mol Biol 304, 2000, pp. 621-632, The TolA-recognition Site of Colicin N. ITC, SPR, and Stopped-flow . . . .

* cited by examiner pTolE
GGTGGGGGATCTGATGATGACGATAAAGGATCCGGTACCTGATGAACGCGT
 G  G  G  S  D  D  D  D  K↑G  S  G  T  *  *  T  R pTolT$_s$
  GGTGGGGGATCTCTGGTTCCGCGCGGATCCGGTACCTGATGAACGCGT
   G  G  G  S  L  V  P  R↑G  S  G  T  *  *  T  R pTolX
  GGTGGGGGATCTATTGAAGGTCGCGGATCCGGTACCTGATGAACGCGT
   G  G  G  S  I  E  G  R↑G  S  G  T  *  *  T  R

SEQUENCE LISTING

<160> NUMBER OF SEQ ID NOS: 61

<210> SEQ ID NO 1
<211> LENGTH: 9
<212> TYPE: PRT
<213> ORGANISM: Artificial Sequence
<220> FEATURE:
<223> OTHER INFORMATION: Ala3-His6 tail

<400> SEQUENCE: 1

Ala Ala Ala His His His His His His
1               5

<210> SEQ ID NO 2
<211> LENGTH: 25
<212> TYPE: PRT
<213> ORGANISM: Escherichia coli

<400> SEQUENCE: 2

Met Asn Met Lys Lys Leu Ala Thr Leu Val Ser Ala Val Ala Leu Ser
1               5                   10                  15

Ala Thr Val Ser Ala Asn Ala Met Ala
            20                  25

```
<210> SEQ ID NO 3
<211> LENGTH: 5
<212> TYPE: PRT
<213> ORGANISM: Artificial Sequence
<220> FEATURE:
<223> OTHER INFORMATION: Cleavage site for enterokinase

<400> SEQUENCE: 3

Asp Asp Asp Asp Lys
1               5

<210> SEQ ID NO 4
<211> LENGTH: 4
<212> TYPE: PRT
<213> ORGANISM: Artificial Sequence
<220> FEATURE:
<223> OTHER INFORMATION: Cleavage site for thrombin

<400> SEQUENCE: 4

Leu Val Pro Arg
1

<210> SEQ ID NO 5
<211> LENGTH: 4
<212> TYPE: PRT
<213> ORGANISM: Artificial Sequence
<220> FEATURE:
<223> OTHER INFORMATION: Cleavage site for factor Xa

<400> SEQUENCE: 5

Ile Glu Gly Arg
1

<210> SEQ ID NO 6
<211> LENGTH: 4
<212> TYPE: PRT
<213> ORGANISM: Artificial Sequence
<220> FEATURE:
<223> OTHER INFORMATION: 4xHis tag

<400> SEQUENCE: 6

His His His His
1

<210> SEQ ID NO 7
<211> LENGTH: 5
<212> TYPE: PRT
<213> ORGANISM: Artificial Sequence
<220> FEATURE:
<223> OTHER INFORMATION: 5xHis tag

<400> SEQUENCE: 7

His His His His His
1               5

<210> SEQ ID NO 8
<211> LENGTH: 6
<212> TYPE: PRT
<213> ORGANISM: Artificial Sequence
<220> FEATURE:
<223> OTHER INFORMATION: 6xHis tag

<400> SEQUENCE: 8

His His His His His His
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: 7xHis tag

<400> SEQUENCE: 9

His His His His His His His
1               5

<210> SEQ ID NO 10
<211> LENGTH: 8
<212> TYPE: PRT
<213> ORGANISM: Artificial Sequence
<220> FEATURE:
<223> OTHER INFORMATION: 8xHis tag

<400> SEQUENCE: 10

His His His His His His His His
1               5

<210> SEQ ID NO 11
<211> LENGTH: 9
<212> TYPE: PRT
<213> ORGANISM: Artificial Sequence
<220> FEATURE:
<223> OTHER INFORMATION: 9xHis tag

<400> SEQUENCE: 11

His His His His His His His His His
1               5

<210> SEQ ID NO 12
<211> LENGTH: 10
<212> TYPE: PRT
<213> ORGANISM: Artificial Sequence
<220> FEATURE:
<223> OTHER INFORMATION: 10xHis tag

<400> SEQUENCE: 12

His His His His His His His His His His
1               5                   10

<210> SEQ ID NO 13
<211> LENGTH: 93
<212> TYPE: PRT
<213> ORGANISM: Escherichia coli

<400> SEQUENCE: 13

Asn Asn Gly Ala Ser Gly Ala Asp Ile Asn Asn Tyr Ala Gly Gln Ile
1               5                   10                  15

Lys Ser Ala Ile Glu Ser Lys Phe Tyr Asp Ala Ser Ser Tyr Ala Gly
                20                  25                  30

Lys Thr Cys Thr Leu Arg Ile Lys Leu Ala Pro Asp Gly Met Leu Leu
            35                  40                  45

Asp Ile Lys Pro Glu Gly Gly Asp Pro Ala Leu Cys Gln Ala Ala Leu
        50                  55                  60

Ala Ala Ala Lys Leu Ala Lys Ile Pro Lys Pro Ser Gln Ala Val
65                  70                  75                  80

Tyr Glu Val Phe Lys Asn Ala Pro Leu Asp Phe Lys Pro
                85                  90

<210> SEQ ID NO 14
```

<211> LENGTH: 348
<212> TYPE: PRT
<213> ORGANISM: Artificial Sequence
<220> FEATURE:
<223> OTHER INFORMATION: TolA-BCL fusion protein

<400> SEQUENCE: 14

```
Met His His His His His Ser Ser Asn Asn Gly Ala Ser Gly Ala
1               5                   10                  15

Asp Ile Asn Asn Tyr Ala Gly Gln Ile Lys Ser Ala Ile Glu Ser Lys
            20                  25                  30

Phe Tyr Asp Ala Ser Ser Tyr Ala Gly Lys Thr Cys Thr Leu Arg Ile
        35                  40                  45

Lys Leu Ala Pro Asp Gly Met Leu Leu Asp Ile Lys Pro Glu Gly Gly
    50                  55                  60

Asp Pro Ala Leu Cys Gln Ala Ala Leu Ala Ala Ala Lys Leu Ala Lys
65                  70                  75                  80

Ile Pro Lys Pro Pro Ser Gln Ala Val Tyr Glu Val Phe Lys Asn Ala
                85                  90                  95

Pro Leu Asp Phe Lys Pro Gly Gly Gly Ser Gly Ser Leu Val Pro Arg
            100                 105                 110

Gly Ser Arg Pro Ser Gln Ser Asn Arg Glu Leu Val Val Asp Phe Leu
        115                 120                 125

Ser Tyr Lys Leu Ser Gln Lys Gly Tyr Ser Trp Ser Gln Phe Ser Asp
    130                 135                 140

Val Glu Glu Asn Arg Thr Glu Ala Pro Glu Gly Thr Glu Ser Glu Met
145                 150                 155                 160

Glu Thr Pro Ser Ala Ile Asn Gly Asn Pro Ser Trp His Leu Ala Asp
                165                 170                 175

Ser Pro Ala Val Asn Gly Ala Thr Ala His Ser Ser Ser Leu Asp Ala
            180                 185                 190

Arg Glu Val Ile Pro Met Ala Ala Val Lys Gln Ala Leu Arg Glu Ala
        195                 200                 205

Gly Asp Glu Phe Glu Leu Arg Tyr Arg Arg Ala Phe Ser Asp Leu Thr
    210                 215                 220

Ser Gln Leu His Ile Thr Pro Gly Thr Ala Tyr Gln Ser Phe Glu Gln
225                 230                 235                 240

Val Val Asn Glu Leu Phe Arg Asp Gly Val Asn Trp Gly Arg Ile Val
                245                 250                 255

Ala Phe Phe Ser Phe Gly Gly Ala Leu Cys Val Glu Ser Val Asp Lys
            260                 265                 270

Glu Met Gln Val Leu Val Ser Arg Ile Ala Ala Trp Met Ala Thr Tyr
        275                 280                 285

Leu Asn Asp His Leu Glu Pro Trp Ile Gln Glu Asn Gly Gly Trp Asp
    290                 295                 300

Thr Phe Val Glu Leu Tyr Gly Asn Asn Ala Ala Ala Glu Ser Arg Lys
305                 310                 315                 320

Gly Gln Glu Arg Phe Asn Arg Trp Phe Leu Thr Gly Met Thr Val Ala
                325                 330                 335

Gly Val Val Leu Leu Gly Ser Leu Phe Ser Arg Lys
            340                 345
```

<210> SEQ ID NO 15
<211> LENGTH: 236
<212> TYPE: PRT
<213> ORGANISM: Artificial Sequence

```
<220> FEATURE:
<223> OTHER INFORMATION: TolA-BCL fusion protein after thrombin cleavage

<400> SEQUENCE: 15

Gly Ser Arg Pro Ser Gln Ser Asn Arg Glu Leu Val Val Asp Phe Leu
1               5                   10                  15

Ser Tyr Lys Leu Ser Gln Lys Gly Tyr Ser Trp Ser Gln Phe Ser Asp
            20                  25                  30

Val Glu Glu Asn Arg Thr Glu Ala Pro Glu Gly Thr Glu Ser Glu Met
        35                  40                  45

Glu Thr Pro Ser Ala Ile Asn Gly Asn Pro Ser Trp His Leu Ala Asp
    50                  55                  60

Ser Pro Ala Val Asn Gly Ala Thr Ala His Ser Ser Leu Asp Ala
65                  70                  75                  80

Arg Glu Val Ile Pro Met Ala Ala Val Lys Gln Ala Leu Arg Glu Ala
                85                  90                  95

Gly Asp Glu Phe Glu Leu Arg Tyr Arg Arg Ala Phe Ser Asp Leu Thr
            100                 105                 110

Ser Gln Leu His Ile Thr Pro Gly Thr Ala Tyr Gln Ser Phe Glu Gln
        115                 120                 125

Val Val Asn Glu Leu Phe Arg Asp Gly Val Asn Trp Gly Arg Ile Val
    130                 135                 140

Ala Phe Phe Ser Phe Gly Gly Ala Leu Cys Val Glu Ser Val Asp Lys
145                 150                 155                 160

Glu Met Gln Val Leu Val Ser Arg Ile Ala Ala Trp Met Ala Thr Tyr
                165                 170                 175

Leu Asn Asp His Leu Glu Pro Trp Ile Gln Glu Asn Gly Gly Trp Asp
            180                 185                 190

Thr Phe Val Glu Leu Tyr Gly Asn Asn Ala Ala Ala Glu Ser Arg Lys
        195                 200                 205

Gly Gln Glu Arg Phe Asn Arg Trp Phe Leu Thr Gly Met Thr Val Ala
    210                 215                 220

Gly Val Val Leu Leu Gly Ser Leu Phe Ser Arg Lys
225                 230                 235

<210> SEQ ID NO 16
<211> LENGTH: 115
<212> TYPE: PRT
<213> ORGANISM: Artificial Sequence
<220> FEATURE:
<223> OTHER INFORMATION: Tagged TolAIII region of pTol vectors
<220> FEATURE:
<221> NAME/KEY: MISC_FEATURE
<222> LOCATION: (107)..(111)
<223> OTHER INFORMATION: Xaa residues represent cleavage sites DDDDK
      (SEQ ID NO: 3), LVPR (SEQ ID NO: 4; no Xaa at position 111) or
      IEGR (SEQ ID NO: 5; no Xaa at position 111)

<400> SEQUENCE: 16

Met His His His His His Ser Ser Asn Asn Gly Ala Ser Gly Ala
1               5                   10                  15

Asp Ile Asn Asn Tyr Ala Gly Gln Ile Lys Ser Ala Ile Glu Ser Lys
            20                  25                  30

Phe Tyr Asp Ala Ser Ser Tyr Ala Gly Lys Thr Cys Thr Leu Arg Ile
        35                  40                  45

Lys Leu Ala Pro Asp Gly Met Leu Leu Asp Ile Lys Pro Glu Gly Gly
    50                  55                  60

Asp Pro Ala Leu Cys Gln Ala Ala Leu Ala Ala Ala Lys Leu Ala Lys
```

```
                65                  70                  75                  80
        Ile Pro Lys Pro Pro Ser Gln Ala Val Tyr Glu Val Phe Lys Asn Ala
                        85                  90                  95

Pro Leu Asp Phe Lys Pro Gly Gly Gly Ser Xaa Xaa Xaa Xaa Xaa Gly
                        100                 105                 110

Ser Gly Thr
                115

<210> SEQ ID NO 17
<211> LENGTH: 8
<212> TYPE: PRT
<213> ORGANISM: Artificial Sequence
<220> FEATURE:
<223> OTHER INFORMATION: His6-Ser2 linker

<400> SEQUENCE: 17

His His His His His His Ser Ser
1               5

<210> SEQ ID NO 18
<211> LENGTH: 4
<212> TYPE: PRT
<213> ORGANISM: Artificial Sequence
<220> FEATURE:
<223> OTHER INFORMATION: Short flexible polypeptide

<400> SEQUENCE: 18

Gly Gly Gly Ser
1

<210> SEQ ID NO 19
<211> LENGTH: 51
<212> TYPE: DNA
<213> ORGANISM: Artificial Sequence
<220> FEATURE:
<223> OTHER INFORMATION: Cleavage/cloning site of pTolE vector

<400> SEQUENCE: 19
ggtgggggat ctgatgatga cgataaagga tccggtacct gatgaacgcg t           51

<210> SEQ ID NO 20
<211> LENGTH: 48
<212> TYPE: DNA
<213> ORGANISM: Artificial Sequence
<220> FEATURE:
<223> OTHER INFORMATION: Cleavage/cloning site of pTolT vector

<400> SEQUENCE: 20
ggtgggggat ctctggttcc gcgcggatcc ggtacctgat gaacgcgt              48

<210> SEQ ID NO 21
<211> LENGTH: 48
<212> TYPE: DNA
<213> ORGANISM: Artificial Sequence
<220> FEATURE:
<223> OTHER INFORMATION: Cleavage/cloning site of pTolX vector

<400> SEQUENCE: 21
ggtgggggat ctattgaagg tcgcggatcc ggtacctgat gaacgcgt              48

<210> SEQ ID NO 22
<211> LENGTH: 17
<212> TYPE: PRT
<213> ORGANISM: Artificial Sequence
<220> FEATURE:
```

```
<223> OTHER INFORMATION: Cleavage/cloning site of pTolE vector
<220> FEATURE:
<221> NAME/KEY: MISC_FEATURE
<222> LOCATION: (14)..(15)
<223> OTHER INFORMATION: Xaa represents stop codon site

<400> SEQUENCE: 22

Gly Gly Gly Ser Asp Asp Asp Asp Lys Gly Ser Gly Thr Xaa Xaa Thr
1               5                   10                  15

Arg

<210> SEQ ID NO 23
<211> LENGTH: 16
<212> TYPE: PRT
<213> ORGANISM: Artificial Sequence
<220> FEATURE:
<223> OTHER INFORMATION: Cleavage/cloning site of pTolT vector
<220> FEATURE:
<221> NAME/KEY: MISC_FEATURE
<222> LOCATION: (13)..(14)
<223> OTHER INFORMATION: Xaa represents stop codon site

<400> SEQUENCE: 23

Gly Gly Gly Ser Leu Val Pro Arg Gly Ser Gly Thr Xaa Xaa Thr Arg
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Cleavage/cloning site of pTolX vector
<220> FEATURE:
<221> NAME/KEY: MISC_FEATURE
<222> LOCATION: (13)..(14)
<223> OTHER INFORMATION: Xaa represents stop codon site

<400> SEQUENCE: 24

Gly Gly Gly Ser Ile Glu Gly Arg Gly Ser Gly Thr Xaa Xaa Thr Arg
1               5                   10                  15

<210> SEQ ID NO 25
<211> LENGTH: 2
<212> TYPE: PRT
<213> ORGANISM: Artificial Sequence
<220> FEATURE:
<223> OTHER INFORMATION: Gly-Ser tag

<400> SEQUENCE: 25

Gly Ser
1

<210> SEQ ID NO 26
<211> LENGTH: 4
<212> TYPE: PRT
<213> ORGANISM: Artificial Sequence
<220> FEATURE:
<223> OTHER INFORMATION: Gly-Ser-Gly-Thr tag

<400> SEQUENCE: 26

Gly Ser Gly Thr
1

<210> SEQ ID NO 27
<211> LENGTH: 39
<212> TYPE: DNA
<213> ORGANISM: Artificial Sequence
<220> FEATURE:
```

<223> OTHER INFORMATION: Synthetic oligonucleotide

<400> SEQUENCE: 27
gatctgatga tgacgataaa ggatccggta cctgatgaa                39

<210> SEQ ID NO 28
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 28
cgcgttcatc aggtaccgga tcctttatcg tcatcatca                39

<210> SEQ ID NO 29
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 29
gatctattga aggtcgcgga tccggtacct gatgaa                36

<210> SEQ ID NO 30
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 30
cgcgttcatc aggtaccgga tccgcgacct tcaata                36

<210> SEQ ID NO 31
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 31
gatctctggt tccgcgcgga tccggtacct gatgaa                36

<210> SEQ ID NO 32
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 32
cgcgttcatc aggtaccgga tccgcgcgga accaga                36

<210> SEQ ID NO 33
<211> LENGTH: 37
<212> TYPE: PRT
<213> ORGANISM: Escherichia coli

<400> SEQUENCE: 33

Asn Ser Asn Gly Trp Ser Trp Ser Asn Lys Pro His Lys Asn Asp Gly
1               5                   10                  15

Phe His Ser Asp Gly Ser Tyr His Ile Thr Phe His Gly Asp Asn Asn
            20                  25                  30

Ser Lys Pro Lys Pro
        35

<210> SEQ ID NO 34
<211> LENGTH: 80
<212> TYPE: PRT
<213> ORGANISM: Escherichia coli

<400> SEQUENCE: 34

Asn Asn Ala Phe Gly Gly Lys Asn Pro Gly Ile Gly Asn Thr Ser
1               5                   10                  15

Gly Ala Gly Ser Asn Gly Ser Ala Ser Ser Asn Arg Gly Asn Ser Asn
                20                  25                  30

Gly Trp Ser Trp Ser Asn Lys Pro His Lys Asn Asp Gly Phe His Ser
            35                  40                  45

Asp Gly Ser Tyr His Ile Thr Phe His Gly Asp Asn Asn Ser Lys Pro
        50                  55                  60

Lys Pro Gly Gly Asn Ser Gly Asn Arg Gly Asn Asn Gly Asp Gly Ala
65                  70                  75                  80

<210> SEQ ID NO 35
<211> LENGTH: 117
<212> TYPE: PRT
<213> ORGANISM: Escherichia coli

<400> SEQUENCE: 35

His Gly Asp Asn Asn Ser Lys Pro Lys Pro Gly Gly Asn Ser Gly Asn
1               5                   10                  15

Arg Gly Asn Asn Gly Asp Gly Ala Ser Ala Lys Val Gly Glu Ile Thr
                20                  25                  30

Ile Thr Pro Asp Asn Ser Lys Pro Gly Arg Tyr Ile Ser Ser Asn Pro
            35                  40                  45

Glu Tyr Ser Leu Leu Ala Lys Leu Ile Asp Ala Glu Ser Ile Lys Gly
        50                  55                  60

Thr Glu Val Tyr Thr Phe His Thr Arg Lys Gly Gln Tyr Val Lys Val
65                  70                  75                  80

Thr Val Pro Asp Ser Asn Ile Asp Lys Met Arg Val Asp Tyr Val Asn
                85                  90                  95

Trp Lys Gly Pro Lys Tyr Asn Asn Lys Leu Val Lys Arg Phe Val Ser
            100                 105                 110

Gln Phe Leu Leu Phe
        115

<210> SEQ ID NO 36
<211> LENGTH: 124
<212> TYPE: PRT
<213> ORGANISM: Homo sapiens

<400> SEQUENCE: 36

Asn Leu Val Asn Phe His Arg Met Ile Lys Leu Thr Thr Gly Lys Glu
1               5                   10                  15

Ala Ala Leu Ser Tyr Gly Phe Tyr Gly Cys His Cys Gly Val Gly Gly
                20                  25                  30

Arg Gly Ser Pro Lys Asp Ala Thr Asp Arg Cys Cys Val Thr His Asp
            35                  40                  45

Cys Cys Tyr Lys Arg Leu Glu Lys Arg Gly Cys Gly Thr Lys Phe Leu
        50                  55                  60

```
Ser Tyr Lys Phe Ser Asn Ser Gly Ser Arg Ile Thr Cys Ala Lys Gln
 65                  70                  75                  80

Asp Ser Cys Arg Ser Gln Leu Cys Glu Cys Asp Lys Ala Ala Thr
                 85                  90                  95

Cys Phe Ala Arg Asn Lys Thr Thr Tyr Asn Lys Lys Tyr Gln Tyr Tyr
                100                 105                 110

Ser Asn Lys His Cys Arg Gly Ser Thr Pro Arg Cys
            115                 120

<210> SEQ ID NO 37
<211> LENGTH: 179
<212> TYPE: PRT
<213> ORGANISM: Actinia equina

<400> SEQUENCE: 37

Ser Ala Asp Val Ala Gly Ala Val Ile Asp Gly Ala Ser Leu Ser Phe
  1               5                  10                  15

Asp Ile Leu Lys Thr Val Leu Glu Ala Leu Gly Asn Val Lys Arg Lys
                 20                  25                  30

Ile Ala Val Gly Val Asp Asn Glu Ser Gly Lys Thr Trp Thr Ala Leu
             35                  40                  45

Asn Thr Tyr Phe Arg Ser Gly Thr Ser Asp Ile Val Leu Pro His Lys
 50                  55                  60

Val Pro His Gly Lys Ala Leu Leu Tyr Asn Gly Gln Lys Asp Arg Gly
 65                  70                  75                  80

Pro Val Ala Thr Gly Ala Val Gly Val Leu Ala Tyr Leu Met Ser Asp
                 85                  90                  95

Gly Asn Thr Leu Ala Val Leu Phe Ser Val Pro Tyr Asp Tyr Asn Trp
                100                 105                 110

Tyr Ser Asn Trp Trp Asn Val Arg Ile Tyr Lys Gly Lys Arg Arg Ala
            115                 120                 125

Asp Gln Arg Met Tyr Glu Glu Leu Tyr Tyr Asn Leu Ser Pro Phe Arg
130                 135                 140

Gly Asp Asn Gly Trp His Thr Arg Asn Leu Gly Tyr Gly Leu Lys Ser
145                 150                 155                 160

Arg Gly Phe Met Asn Ser Ser Gly His Ala Ile Leu Glu Ile His Val
                165                 170                 175

Ser Lys Ala

<210> SEQ ID NO 38
<211> LENGTH: 191
<212> TYPE: PRT
<213> ORGANISM: Homo sapiens

<400> SEQUENCE: 38

Thr Gly Ala Gly Lys Thr Ser Leu Leu Met Met Ile Met Gly Glu Leu
  1               5                  10                  15

Glu Pro Ser Glu Gly Lys Ile Lys His Ser Gly Arg Ile Ser Phe Cys
                 20                  25                  30

Ser Gln Phe Ser Trp Ile Met Pro Gly Thr Ile Lys Glu Asn Ile Ile
             35                  40                  45

Phe Gly Val Ser Tyr Asp Glu Tyr Arg Tyr Arg Ser Val Ile Lys Ala
 50                  55                  60

Cys Gln Leu Glu Glu Asp Ile Ser Lys Phe Ala Glu Lys Asp Asn Ile
 65                  70                  75                  80

Val Leu Gly Glu Gly Gly Ile Thr Leu Ser Gly Gly Gln Arg Ala Arg
```

-continued

```
                    85                  90                  95
Ile Ser Leu Ala Arg Ala Val Tyr Lys Asp Ala Asp Leu Tyr Leu Leu
            100                 105                 110

Asp Ser Pro Phe Gly Tyr Leu Asp Val Leu Thr Glu Lys Glu Ile Phe
            115                 120                 125

Glu Ser Cys Val Cys Lys Leu Met Ala Asn Lys Thr Arg Ile Leu Val
            130                 135                 140

Thr Ser Lys Met Glu His Leu Lys Lys Ala Asp Lys Ile Leu Ile Leu
145                 150                 155                 160

His Glu Gly Ser Ser Tyr Phe Tyr Gly Thr Phe Ser Glu Leu Gln Asn
                165                 170                 175

Leu Gln Pro Asp Phe Ser Ser Lys Leu Met Gly Cys Asp Ser Phe
            180                 185                 190
```

<210> SEQ ID NO 39
<211> LENGTH: 390
<212> TYPE: PRT
<213> ORGANISM: Homo sapiens

<400> SEQUENCE: 39

```
Lys Tyr Ile Glu His Phe Ser Lys Phe Ser Pro Ser Pro Leu Ser Met
1               5                   10                  15

Lys Gln Phe Leu Asp Phe Gly Ser Ser Asn Ala Cys Glu Lys Thr Ser
            20                  25                  30

Phe Thr Phe Leu Arg Gln Glu Leu Pro Val Arg Leu Ala Asn Ile Met
        35                  40                  45

Lys Glu Ile Asn Leu Leu Pro Asp Arg Val Leu Ser Thr Pro Ser Val
    50                  55                  60

Gln Leu Val Gln Ser Trp Tyr Val Gln Ser Leu Leu Asp Ile Met Glu
65                  70                  75                  80

Phe Leu Asp Lys Asp Pro Glu Asp His Arg Thr Leu Ser Gln Phe Thr
                85                  90                  95

Asp Ala Leu Val Thr Ile Arg Asn Arg His Asn Asp Val Val Pro Thr
            100                 105                 110

Met Ala Gln Gly Val Leu Glu Tyr Lys Asp Thr Tyr Gly Asp Asp Pro
            115                 120                 125

Val Ser Asn Gln Asn Ile Gln Tyr Phe Leu Asp Arg Phe Tyr Leu Ser
            130                 135                 140

Arg Ile Ser Ile Arg Met Leu Ile Asn Gln His Thr Leu Ile Phe Asp
145                 150                 155                 160

Gly Ser Thr Asn Pro Ala His Pro Lys His Ile Gly Ser Ile Asp Pro
                165                 170                 175

Asn Cys Asn Val Ser Glu Val Val Lys Asp Ala Tyr Asp Met Ala Lys
            180                 185                 190

Leu Leu Cys Asp Lys Tyr Tyr Met Ala Ser Pro Asp Leu Glu Ile Gln
            195                 200                 205

Glu Ile Asn Ala Ala Asn Ser Lys Gln Pro Ile His Met Val Tyr Val
            210                 215                 220

Pro Ser His Leu Tyr His Met Leu Phe Glu Leu Phe Lys Asn Ala Met
225                 230                 235                 240

Arg Ala Thr Val Glu Ser His Glu Ser Ser Leu Ile Leu Pro Pro Ile
                245                 250                 255

Lys Val Met Val Ala Leu Gly Glu Glu Asp Leu Ser Ile Lys Met Ser
            260                 265                 270
```

```
Asp Arg Gly Gly Gly Val Pro Leu Arg Lys Ile Glu Arg Leu Phe Ser
        275                 280                 285

Tyr Met Tyr Ser Thr Ala Pro Thr Pro Gln Pro Gly Thr Gly Gly Thr
        290                 295                 300

Pro Leu Ala Gly Phe Gly Tyr Gly Leu Pro Ile Ser Arg Leu Tyr Ala
305                 310                 315                 320

Lys Tyr Phe Gln Gly Asp Leu Gln Leu Phe Ser Met Glu Gly Phe Gly
                325                 330                 335

Thr Asp Ala Val Ile Tyr Leu Lys Ala Leu Ser Thr Asp Ser Val Glu
                340                 345                 350

Arg Leu Pro Val Tyr Asn Lys Ser Ala Trp Arg His Tyr Gln Thr Ile
            355                 360                 365

Gln Glu Ala Gly Asp Trp Cys Val Pro Ser Thr Glu Pro Lys Asn Thr
370                 375                 380

Ser Thr Tyr Arg Val Ser
385                 390

<210> SEQ ID NO 40
<211> LENGTH: 202
<212> TYPE: PRT
<213> ORGANISM: Bacillus licheniformis

<400> SEQUENCE: 40

Ser Phe Ser Glu Leu Asn Ile Asp Ala Phe Arg Phe Ile Asn Asp Leu
1               5                   10                  15

Gly Lys Glu Tyr Ser Met Leu Asn Pro Val Val Tyr Phe Leu Ala Glu
            20                  25                  30

Tyr Met Met Tyr Phe Leu Ala Leu Gly Leu Val Val Tyr Trp Leu Thr
        35                  40                  45

Arg Thr Thr Lys Asn Arg Leu Met Val Ile Tyr Ala Val Ile Ala Phe
    50                  55                  60

Val Val Ala Glu Ile Leu Gly Lys Ile Met Gly Ser Leu His Ser Asn
65                  70                  75                  80

Tyr Gln Pro Phe Ala Thr Leu Pro Asn Val Asn Lys Leu Ile Glu His
                85                  90                  95

Glu Ile Asp Asn Ser Phe Pro Ser Asp His Thr Ile Leu Phe Phe Ser
            100                 105                 110

Ile Gly Phe Leu Ile Phe Leu Phe His Lys Lys Thr Gly Trp Leu Trp
        115                 120                 125

Leu Val Leu Ala Phe Ala Val Gly Ile Ser Arg Ile Trp Ser Gly Val
    130                 135                 140

His Tyr Pro Leu Asp Val Ala Ala Gly Ala Leu Leu Gly Val Leu Ser
145                 150                 155                 160

Ala Leu Phe Val Phe Trp Thr Ala Pro Lys Leu Ser Phe Ile His Gln
                165                 170                 175

Met Leu Ser Leu Tyr Glu Lys Val Glu Gln Arg Ile Val Pro Ser Lys
            180                 185                 190

Asn Lys Ser Asn Asp Lys Ser Lys Asn Phe
        195                 200

<210> SEQ ID NO 41
<211> LENGTH: 354
<212> TYPE: PRT
<213> ORGANISM: Homo sapiens

<400> SEQUENCE: 41
```

```
Gln Arg Ser Pro Leu Glu Lys Ala Ser Val Val Ser Lys Leu Phe Phe
1               5                   10                  15

Ser Trp Thr Arg Pro Ile Leu Arg Lys Gly Tyr Arg Gln Arg Leu Glu
            20                  25                  30

Leu Ser Asp Ile Tyr Gln Ile Pro Ser Val Asp Ser Ala Asp Asn Leu
        35                  40                  45

Ser Glu Lys Leu Glu Arg Glu Trp Asp Arg Glu Leu Ala Ser Lys Lys
50                  55                  60

Asn Pro Lys Leu Ile Asn Ala Leu Arg Arg Cys Phe Phe Trp Arg Phe
65                  70                  75                  80

Met Phe Tyr Gly Ile Phe Leu Tyr Leu Gly Glu Val Thr Lys Ala Val
            85                  90                  95

Gln Pro Leu Leu Leu Gly Arg Ile Ile Ala Ser Tyr Asp Pro Asp Asn
            100                 105                 110

Lys Glu Glu Arg Ser Ile Ala Ile Tyr Leu Gly Ile Gly Leu Cys Leu
            115                 120                 125

Leu Phe Ile Val Arg Thr Leu Leu Leu His Pro Ala Ile Phe Gly Leu
130                 135                 140

His His Ile Gly Met Gln Met Arg Ile Ala Met Phe Ser Leu Ile Tyr
145                 150                 155                 160

Lys Lys Thr Leu Lys Leu Ser Ser Arg Val Leu Asp Lys Ile Ser Ile
            165                 170                 175

Gly Gln Leu Val Ser Leu Leu Ser Asn Asn Leu Asn Lys Phe Asp Glu
            180                 185                 190

Gly Leu Ala Leu Ala His Phe Val Trp Ile Ala Pro Leu Gln Val Ala
            195                 200                 205

Leu Leu Met Gly Leu Ile Trp Glu Leu Leu Gln Ala Ser Ala Phe Cys
210                 215                 220

Gly Leu Gly Phe Leu Ile Val Leu Ala Leu Phe Gln Ala Gly Leu Gly
225                 230                 235                 240

Arg Met Met Met Lys Tyr Arg Asp Gln Arg Ala Gly Lys Ile Ser Glu
            245                 250                 255

Arg Leu Val Ile Thr Ser Glu Met Ile Glu Asn Ile Gln Ser Val Lys
            260                 265                 270

Ala Tyr Cys Trp Glu Glu Ala Met Glu Lys Met Ile Glu Asn Leu Arg
            275                 280                 285

Gln Thr Glu Leu Lys Leu Thr Arg Lys Ala Ala Tyr Val Arg Tyr Phe
            290                 295                 300

Asn Ser Ser Ala Phe Phe Phe Ser Gly Phe Phe Val Val Phe Leu Ser
305                 310                 315                 320

Val Leu Pro Tyr Ala Leu Ile Lys Gly Ile Ile Leu Arg Lys Ile Phe
            325                 330                 335

Thr Thr Ile Ser Phe Cys Ile Val Leu Arg Met Ala Val Thr Arg Gln
            340                 345                 350

Phe Pro

<210> SEQ ID NO 42
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 42
tttttggatc caattccaat ggatggtcat ggag                           34
```

<210> SEQ ID NO 43
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 43
aaggatccaa gcttcaaggt ttaggctttg aattattgtc c            41

<210> SEQ ID NO 44
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 44
tttttggatc caatgctttt ggtggaggga aaaatc                  36

<210> SEQ ID NO 45
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 45
ctcagcggtg gcagcagcc                                     19

<210> SEQ ID NO 46
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 46
cgcggatccc atggggacaa taattcaaag c                       31

<210> SEQ ID NO 47
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 47
ggcgaattca cgcgttaaaa taataatttc tggctcac                38

<210> SEQ ID NO 48
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 48
ccggggtacc aatttggtga atttccacag aatgatc                 37

<210> SEQ ID NO 49
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 49
ggcgaattca cgcgttagca acgaggggtg ctccc                                35

<210> SEQ ID NO 50
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 50
cgcggatccg cagacgtggc tggcgcc                                         27

<210> SEQ ID NO 51
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 51
ggcgaattca cgcgttaagc tttgctcacg tgagtttc                             38

<210> SEQ ID NO 52
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 52
cgcggatcct ctaatggtga tgacagcctc                                      30

<210> SEQ ID NO 53
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 53
ggcgaattca cgcgttagaa agaatcacat cccatgag                             38

<210> SEQ ID NO 54
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 54
ccggggtacc aagtacatag agcacttcag caagttc                              37

<210> SEQ ID NO 55
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 55
ggcgaattca cgcgttacgt gacgcggtac gtggtcg                              37

```
<210> SEQ ID NO 56
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 56
cgcggatcct tttcagaatt aaatattgat g                                    31

<210> SEQ ID NO 57
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 57
ggcgaattca cgcgttaaaa gttcttcgat ttatcg                               36

<210> SEQ ID NO 58
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 58
cgcggatccc agaggtcgcc tctgg                                           25

<210> SEQ ID NO 59
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 59
ggcgaattca cgcgttaggg aaattgccga gtgac                                35

<210> SEQ ID NO 60
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 60 tttttttaggc cttctcagag caaccgggag                                     30

<210> SEQ ID NO 61
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 61
ttttacgcgt tcatttccga ctgaagag                                        28
```

FUSION PROTEINS

This is a National Stage entry under 35 U.S.C. §371 of PCT Application No. PCT/GB03/000078 filed Jan. 10, 2003, published in English.

The present invention relates to fusion proteins (fusion polypeptides), particularly for use in expression and/or purification systems.

Purified proteins are required for several applications. However, the isolation of pure proteins, in sufficient quantities, is sometimes problematic. For protein function studies, large amounts of a protein of interest (for example, a mutated protein) are often needed. Various expression systems have been used for heterologous production of proteins. *Escherichia coli* (*E. coli*) is still the most common host despite huge advances in the area of protein expression in the last ten years in other hosts. *E. coli* is popular because expressing proteins in the bacterium is relatively simple and a vast amount of knowledge about bacterium itself exists, and (sometimes most importantly) because of the low costs associated with production.

Proteins can be expressed in *E. coli* either directly or as fusions (of a "fusion partner" and a protein or polypeptide), also known as fusion proteins. The purpose of fusion partners is to provide affinity tags (e.g. $His_n$ tag, glutathione-S-transferase, cellulose binding domain, intein tags), to make proteins more soluble (e.g. glutathione-S-transferase), to enable formation of disulphide bonds (e.g. thioredoxin), or to export fused proteins to the periplasm where conditions for the formation of disulphide bonds are more favourable (e.g. DsbA and DsbC). Proteins used as fusion partners are normally small (less than 30 kDa).

TolA is a periplasmic protein involved in (1) maintaining the integrity of the inner membrane and (2) the uptake of colicins and bacteriophages. The first function is evidenced by the increased outer membrane instability (e.g. SDS sensitivity) of TolA mutants. This function has been shown by various authors and may depend upon the interaction with the TolB protein (Levengood-Freyermuth et al., 1993, J. Bacteriol. 175: 222-228; Wan & Baneyx, 1998, Protein Expression & Purification 14: 13-22). Wan and Banex (1998, supra) have demonstrated that co-expression of the C-terminal TolAIII domain of TolA (see below) facilitates the recovery of periplasmic recombinant proteins into the growth medium of *E. coli*, confirming that overproduction of the TolAIII domain disrupts the outer membrane and causes periplasmic proteins to leach into the growth medium.

The second function of TolA is based upon the use of TolA as a receptor by phage proteins (Lubkowski, J. et al., 1999, Structure With Folding & Design 7: 711-722) and colicins (Gokce, I. et al., 2000, J. Mol. Biol. 304: 621-632). This has been revealed both by the phage/colicin resistance of tolA mutants and by direct demonstration of the tolA -protein interactions by physical methods. TolA is composed of three domains. A short N-terminal domain is composed of a single transmembrane helix, which anchors TolA in the inner membrane. The second, largest domain is polar and mainly α-helical. A C-terminal domain III (TolAIII) is small and composed of 92 amino acids. Its 3D structure was recently solved in a complex with N1 domain of minor coat gene 3 protein of Ff filamentous bacteriophage (Holliger, P. et al., 1999, J. Mol. Biol. 288: 649-657). It is tightly folded into a slightly elongated protein with the aid of one disulphide bond (FIG. 1).

Lubkowski et al. (1999; supra) disclose a fusion protein comprising residues 1-86 (the N1 domain) of the filamentous Ff bacteriophage minor coat gene 3 protein g3p towards the N-terminus and residues 295-425 (including the TolAIII domain) of TolA, a coreceptor of g3p, towards the C-terminus, and a C-terminal $Ala_3His_6$ (SEQ ID NO: 1) tail. The fusion protein was used by Lubkowski et al. to elucidate the crystal structure of a complex formed between the g3p N1 and TolAIII domains.

Various homologues of the TolA protein are known, for example from *E. coli* (SwissProt Acc. No. P19934), *Salmonella* species (for example Genbank Acc. Nos gi16764117 and gi1675986, *Pectobacterium* species (for example Genbank Acc. No. gi16116636) and *Haemophilus* species (for example Genbank Acc. No. gi2126342).

The present inventors have found that the TolAIII domain has remarkable properties which are of particular use as a fusion protein partner to achieve high levels of expression in a host cell.

According to the present invention, there is provided a fusion polypeptide for expression in a host cell comprising a TolAIII domain or a functional homologue, fragment, or derivative thereof and a non-TolA polypeptide, wherein the TolAIII domain or functional homologue, fragment, or derivative thereof is located towards the N-terminus of the fusion polypeptide and the non-TolA polypeptide is located towards the C-terminus of the fusion polypeptide.

As used herein, the terms "polypeptide" and "protein" are synonymous and refer to a sequence of two or more linked amino acid residues.

The TolAIII domain, when located towards the N-terminus of a fusion polypeptide, has been shown by the present inventors to facilitate higher than expected levels of the TolAIII fusion polypeptide expression in a host cell. The TolAIII domain fusions will be useful, for example, for obtaining purified protein and polypeptide partners and/or for studying the properties of these partners.

The fusion polypeptide may further comprise a signal peptide. This will allow the fusion polypeptide to be targeted to a specific intra- or extra-cellular location. The signal peptide may be located at or near the N-terminus of the fusion polypeptide. The signal peptide may be cleaved from the fusion polypeptide during the targetting process.

If the fusion polypeptide has the basic structure: N terminus-TolAIII-Protein partner-C terminus, it may be expected that it will be expressed in high yields in the cytoplasm. If, however, the fusion polypeptide has the basic structure: N terminus-Signal peptide-TolAIII-Protein partner-C terminus, the signal peptide may be used to target the construct to a non-cytoplasmic location. For example, in *E. coli* expression systems the ribose-binding-protein signal peptide (for example, the *E. coli* ribose-binding-protein signal peptide [SEQ ED NO: 2]) may be used to target a fusion protein to the periplasm. Signal peptides which may be suitable for use in the present invention conform to a set of general rules which are described in Von Heijne, G. 1985, J. Mol. Biol. 184 (1): 99-105.

The TolAIII domain or functional homologue, fragment, or derivative thereof may be codon-optimised for expression in the host cell.

The fusion polypeptide may further comprise a linker between the TolAIII domain or functional homologue, fragment, or derivative thereof and the non-TolA polypeptide. The linker may provide a physical separation between the TolAIII domain or functional homologue, fragment, or derivative thereof and the non-TolA polypeptide or may be functional. The linker may comprise at least one cleavage site for an endopeptidase. For example, the cleavage site may comprise the amino acid sequence DDDDK (SEQ ID NO: 3; for enterokinase) and/or LVPR (SEQ ID NO: 4; for thrombin) and/or IEGR (SEQ ID NO: 5; for factor Xa).

In one embodiment, the fusion polypeptide according to invention may further comprise an affinity purification tag. The affinity purification tag may be located at or near the N-terminus of the fusion polypeptide. For example, the affinity purification tag is an N-terminal $His_n$ tag, with n=4, 5, 6, 7, 8, 9 or 10 (SEQ ID NOs: 6-12, respectively; preferably n=6 [SEQ ID NO: 8]), optionally with the $His_n$ tag linked to the fusion polypeptide by one or more Ser residues (preferably two). The affinity purification tag will provide one means for immobilising the fusion polypeptide, for example as a step in purification.

In one embodiment, the fusion polypeptide comprises a signal peptide at the N-terminus and an affinity purification tag near the N-terminus. If the signal peptide is cleaved from the fusion polypeptide during targeting, then the affinity purification tag may be located at or nearer to the new N-terminus of the fusion protein.

Preferably, the TolAIII domain consists of amino acid residues 329-421 (SEQ ID NO: 13) of *Escherichia coli* TolA (SwissProt Acc. No. P19934).

The host cell may be bacterial (for example, *Escherichia coli*).

The non-TolA polypeptide of the fusion polypeptide may be human BCL-XL (SEQ ID NO: 62, SWISSPROT Accession No. B47537). The fusion polypeptide with human BCL-XL (SEQ ID NO: 62) may comprise the amino acid sequence of SEQ ID NO: 14 or SEQ ID NO: 15. As shown in Example 2 below, large amounts of BCL-XL (SEQ ID NO: 62, an important protein in apoptosis and cancer research) can be generated by expression as a TolAIII fusion polypeptide.

Further provided according to the present invention is a DNA molecule encoding the fusion polypeptide as defined above. The mRNA properties of the DNA molecule when transcribed may be optimised for expression in the host cell.

Also provided is an expression vector comprising the DNA molecule as defined above for expression of the fusion polypeptide of the invention. The expression vector may have an inducible promoter (for example, the IPTG-inducible T7 promotor) which drives expression of the fusion polypeptide. The expression vector may also have an antibiotic resistance marker (for example, the bla gene, which confers resistance to ampicillin and chloramphenicol).

In another aspect of the invention there is provided a cloning vector for producing the expression vector as defined above, comprising DNA encoding the TolAIII domain or a functional homologue, fragment, or derivative thereof upstream or downstream from a cloning site which allows in-frame insertion of DNA encoding a non-TolA polypeptide. The cloning vector may further comprise DNA encoding at least one cleavage site (for example, the amino acid sequence DDDDK [SEQ ID NO: 3] and/or LVPR [SEQ ID NO: 4] and/or IEGR [SEQ ID NO: 5]) for an endopeptidase, the cleavage site located between the DNA encoding the TolAIII domain or a functional homologue, fragment, or derivative thereof and the cloning site. The cloning site may comprise at least one restriction endonuclease (for example, BamHI and/or KpnI) target sequence. The cloning vector may further comprise DNA encoding an affinity purification tag as defined above. The cloning vector may further comprise an inducible promoter (for example, the IPTG-inducible T7 promotor) and/or DNA encoding an antibiotic resistance marker (for example, the bla gene, which confers resistance to ampicillin and chloramphenicol).

Figure 2:
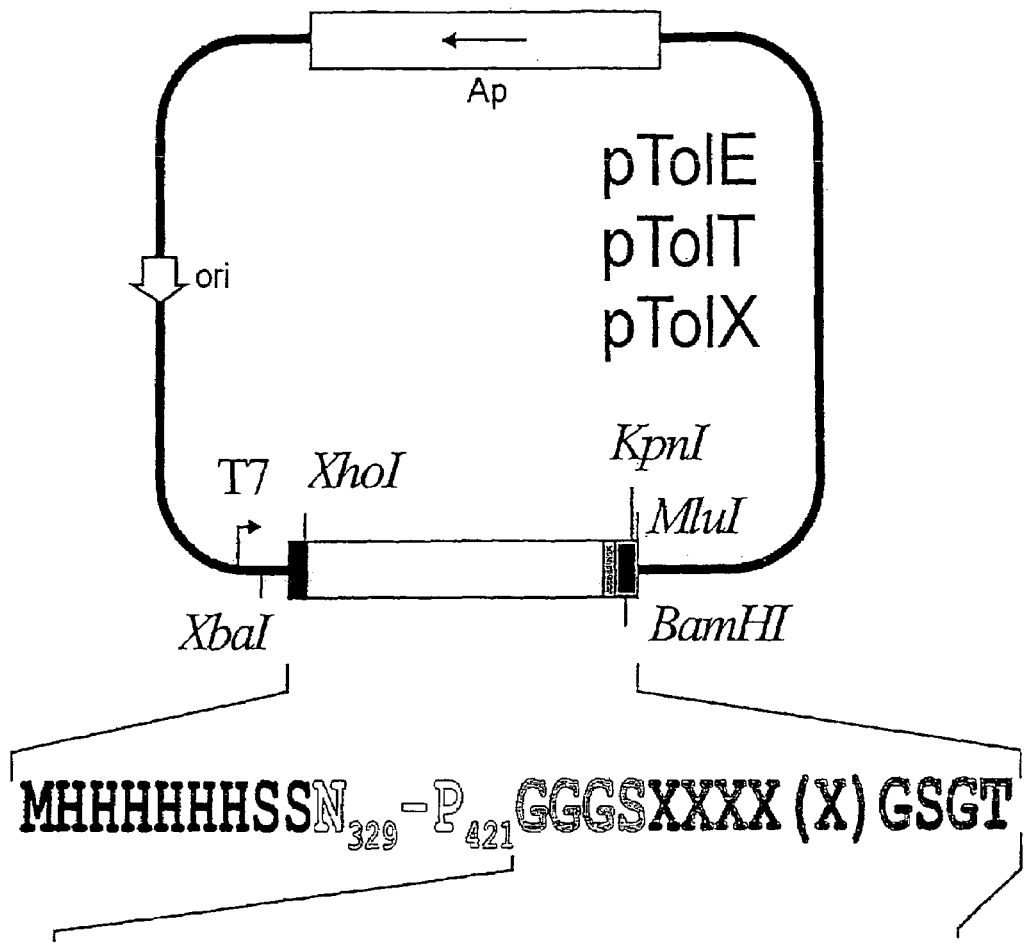

For example, the cloning vector may have the structure of pTolE, pTolT or pTolX (as shown in FIG. 2 with reference to the description).

Also provided is the use of the TolAIII domain or functional homologue, fragment, or derivative thereof for production of a fusion polypeptide as defined above.

Further provided is the use of the TolAIII domain or functional homologue, fragment, or derivative thereof for production of the DNA molecule as defined above.

Yet further provided is the use of the TolAIII domain or functional homologue, fragment, or derivative thereof for production of an expression vector as defined above.

Also provided is the use of the TolAIII domain or functional homologue, fragment, or derivative thereof for production of a cloning vector as defined above.

In one aspect there is provided a host cell containing the DNA as defined above and/or the expression vector as defined above and/or the cloning vector as defined above.

In another aspect there is provided the use of the fusion polypeptide as defined above for immobilisation of the non-TolA polypeptide, comprising the step of:

binding the fusion polypeptide to a TolA binding polypeptide (eg. the TolA-recognition site of colicin N [Gokce et al., 2000, supra] or other colicins, the TolA binding region of bacteriophage g3p-D1 protein [Riechmann & Holliger, 1997, Cell 90: 351-360], or the TolA binding region of TolB or other Tolproteins).

It is known that TolAIII interacts specifically with several naturally occurring proteins such as colicins, phage proteins and other Tolproteins. This range of existing binding partners makes the over expression of TolAIII fusion proteins of particular utility since these proteins may be used in purification or immobilisation technologies. The TolAIII domain therefore not only drives high expression of the fusion polypeptide but also provides an affinity tag for purification, immobilisation or analysis of the fusion polypeptide. The TolAIII binding proteins (or binding polypeptide domains thereof) could be used to provide binding sites for the TolAIII fusions (as in FIG. 6). Protein chips could be made using these TolAIII binding proteins which then bind the TolAIII fusion proteins. This provides a way to immobilise a wide variety of proteins on the surface using the TolAIII fusion as the common interaction.

Alternatively, the fusion polypeptide comprising an affinity tag as defined above may be used for immobilisation of the non-TolA polypeptide, comprising the step of:

binding the affinity tag of the fusion polypeptide to a binding moiety.

Also provided is the use of the fusion polypeptide as defined above for purification and isolation of the non-TolA polypeptide, comprising the steps of:

(i) binding the fusion polypeptide to a TolA binding polypeptide (eg. the TolA-recognition site of colicin N or other colicins, the TolA binding region of bacteriophage g3p-D1 protein, or the TolA binding region of TolB or other Tol proteins);

(ii) cleaving the non-TolA polypeptide from the TolAIII domain or functional homologue, fragment, or derivative thereof using an endopeptidase; and (iii) separating the cleaved non-TolA polypeptide from the TolAIII domain or functional homologue, fragment, or derivative thereof.

In an alternative embodiment, the fusion polypeptide comprising an affinity tag may be used for purification and isolation of the non-TolA polypeptide, comprising the steps of:

(i) binding the affinity tag of the fusion polypeptide to a binding moiety;
(ii) cleaving the non-TolA polypeptide from the TolAIII domain or functional homologue, fragment, or derivative thereof using an endopeptidase; and
(iii) separating the cleaved non-TolA polypeptide from the TolAIII domain or functional homologue, fragment, or derivative thereof.

The fusion polypeptide as disclosed herein may be used for studying interaction properties of the non-TolA polypeptide or the fusion polypeptide, for example self-interaction, interaction with another molecule, or interaction with a physical stimulus.

Also provided is a method for high expression of a polypeptide as a fusion polypeptide in a host cell, comprising the step of expressing the polypeptide as a fusion polypeptide as defined above in a host cell. Levels of expression of a polypeptide as a fusion protein defined herein will be high relative to levels of expression of a polypeptide not linked to the TolAIII domain.

Figure 3:
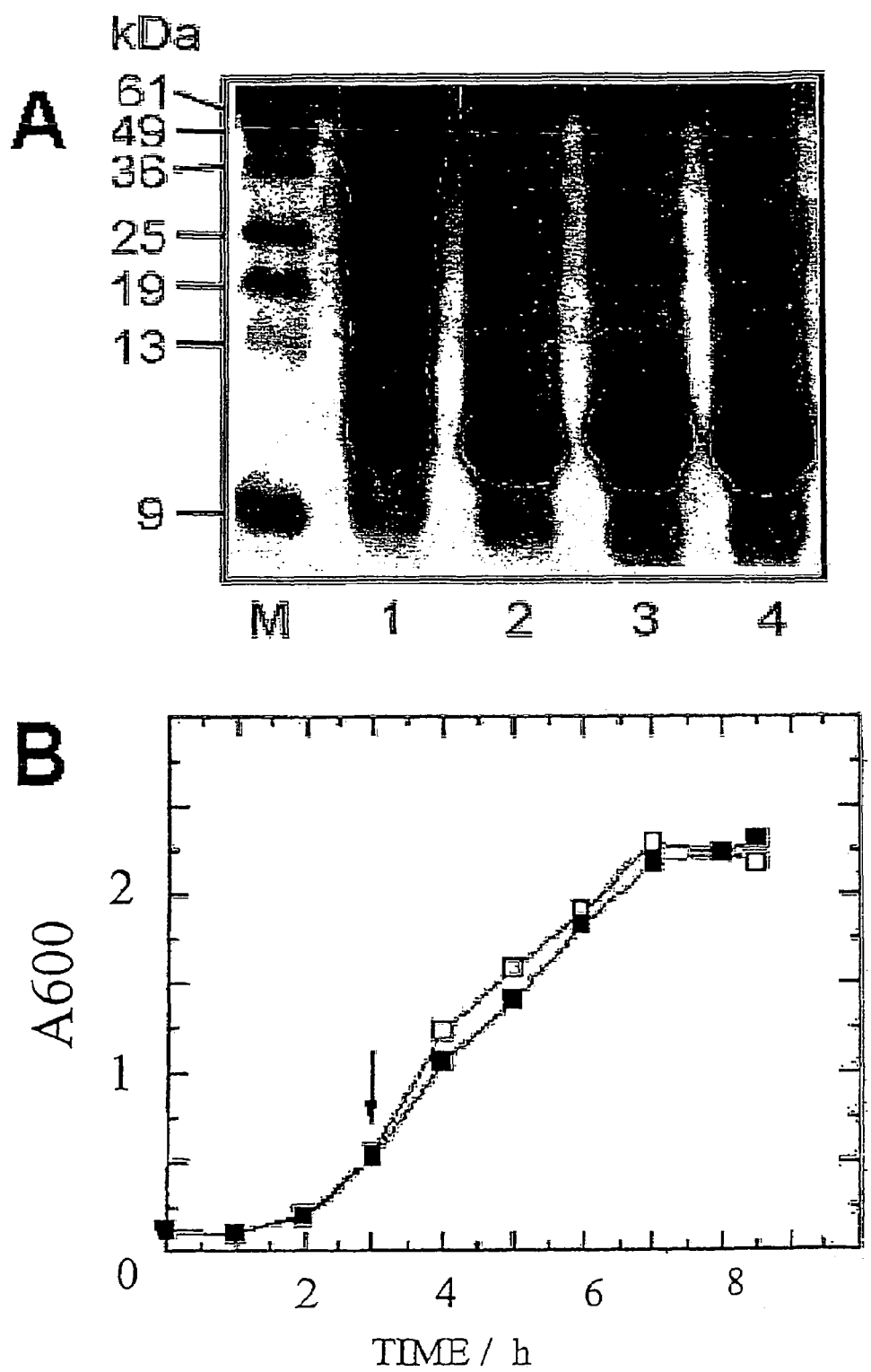
Figure 3:
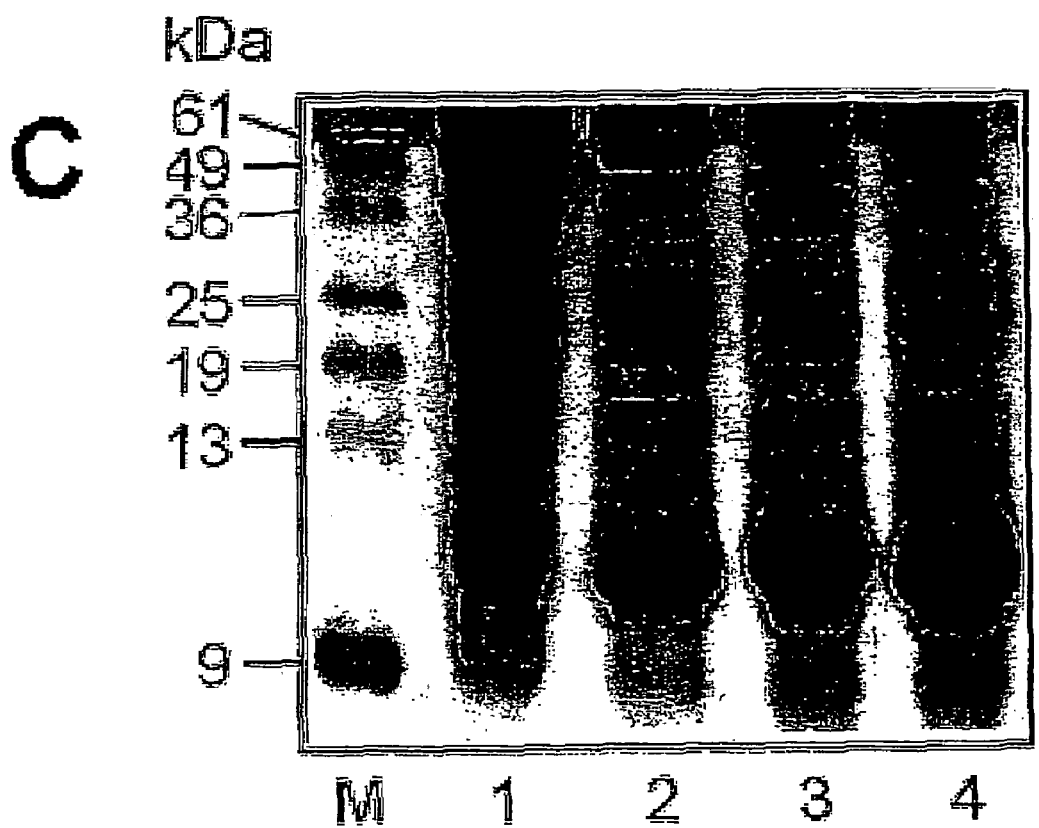
Figure 4:
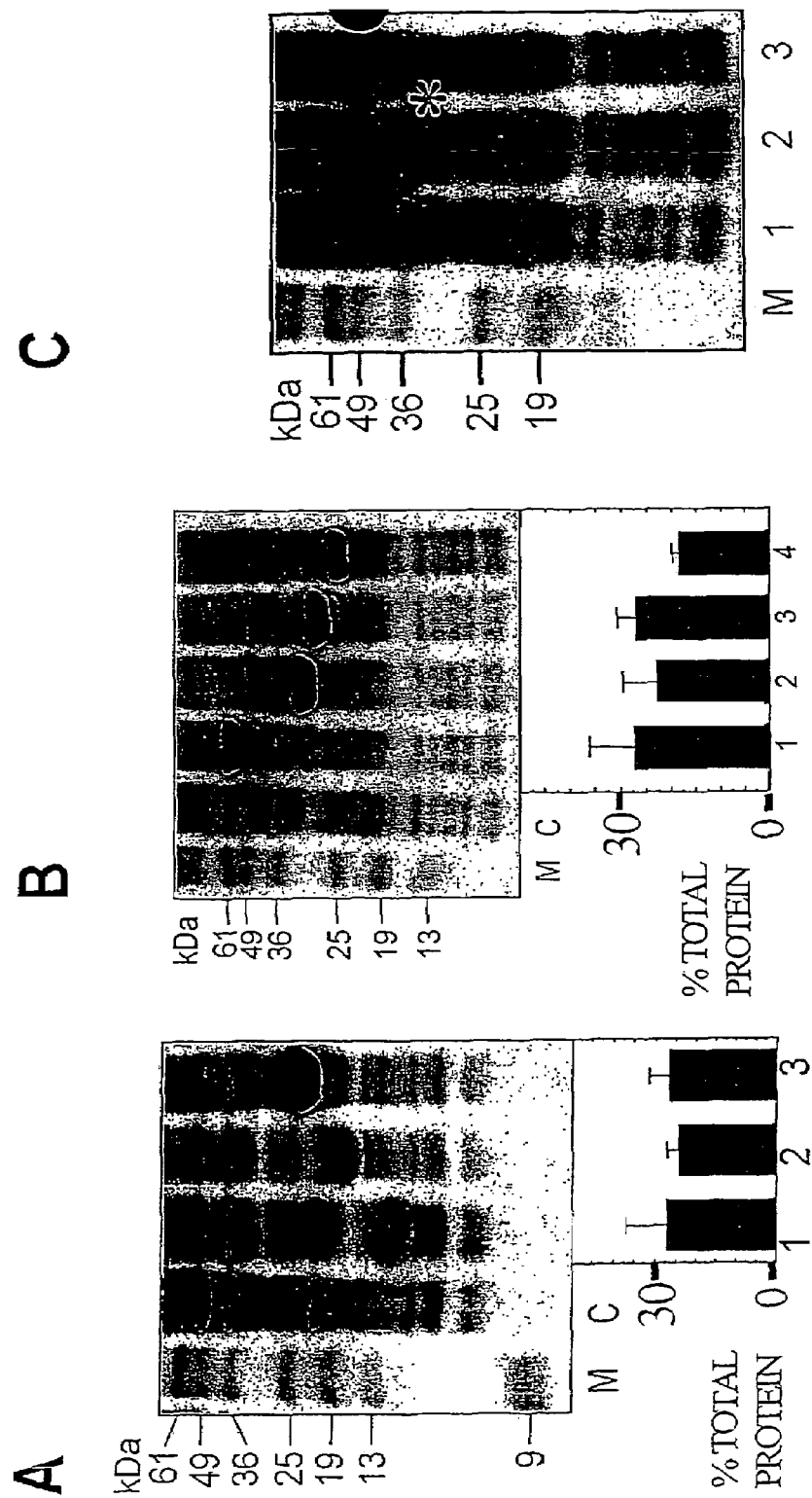
Figure 5:
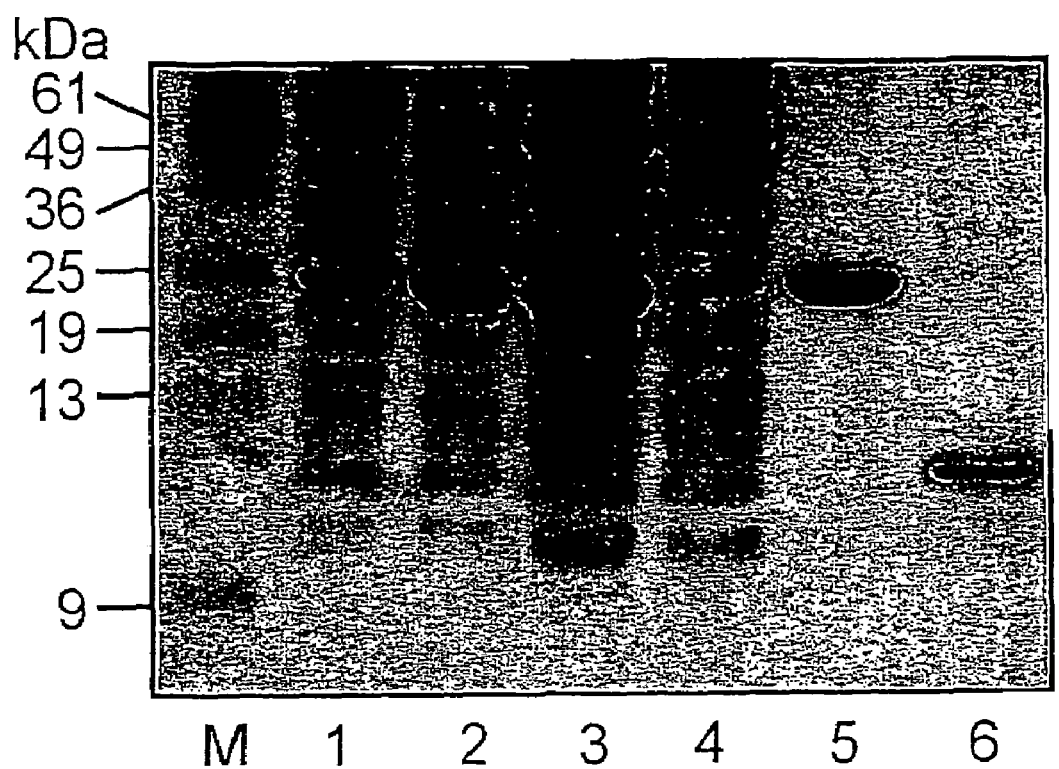
Figure 6:
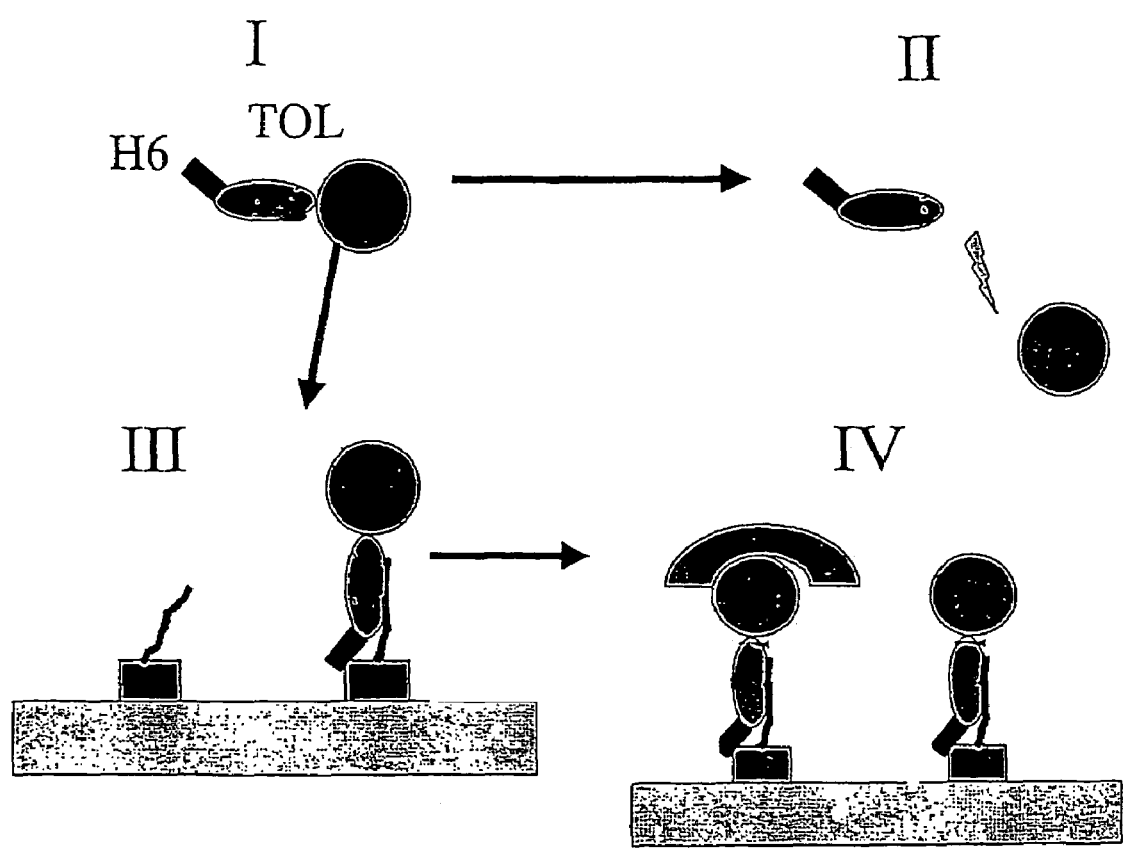
Figure 7:
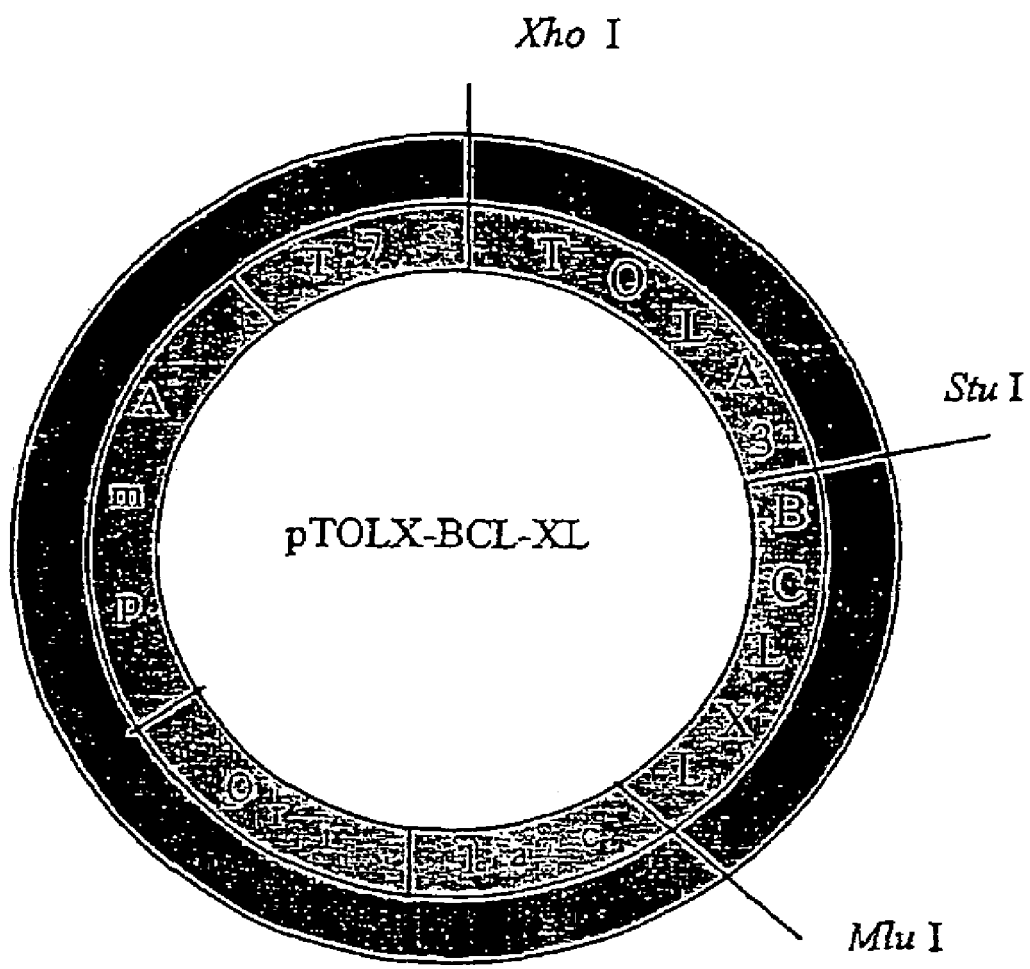
Figure 8:
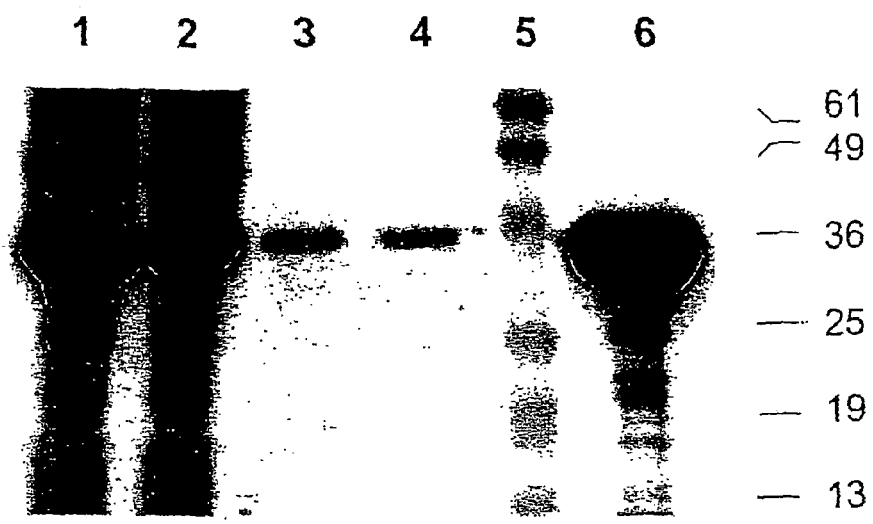

The invention will be further described with reference to the accompanying figures. Of the figures:

FIG. 1: (Prior art) Shows the structure and sequence of third domain of TolA. The model is from the crystal structure of complex between TolAIII and N1 domain of minor coat gene 3 protein from filamentous bacteriophage (Holliger et al., 1999, supra). Disulphide bond is labelled black. Residues 333-421 were resolved in the model;

FIG. 2: Shows pTol expression vectors. pTol vectors are T7 based expression vectors derived from pET8c. The tagged TolAIII region, depicted generically in the middle panel sequence (SEQ ID NO: 16), is inserted in between XhoI and MluI sites. $His_6$-$Ser_2$ linker (SEQ ID NO: 17) precedes the TolA gene for domain III, coding for TolA amino acids 329-421 (SEQ ID NO: 13). Short flexible part (Gly-Gly-Gly-Ser; SEQ ID NO: 18) then follows and the cleavage site for endopeptidases composed of four or five amino acids (denoted by X in middle panel and underlined in bottom panel). The bottom panel shows the DNA sequences (SEQ ID NOs: 19-21, respectively) and encoded amino acid residues (SEQ ID NOs: 22-24, respectively) of the cleavage/cloning site of the tagged TolAIII region of pTolE, pTolT and pTolX. The cleavage site is denoted by an arrow. Stop codons are shown as asterisks;

FIG. 3: Characterization of TolAIII expression. A: SDS-PAGE of expressed TolAIII from using three different vectors. Lane 1, pTolT uninduced; lane 2, pTolX; lane 3, pTolE; lane 4, pTolT. B: Growth curve of bacteria with pTolT. Uninduced (solid squares) sample, induced (open squares) sample. 1 mM IPTG was added to induce sample at the time denoted by an arrow. C: SDS-PAGE of fractionation of bacteria after expression of TolAIII from pTolT. Lane 1, uninduced sample; lane 2, induced bacteria; lane 3, periplasmic fraction; lane 4, cytoplasmic fraction; lane 5, insoluble (membrane+inclusion bodies) fraction. M, molecular weight marker;

FIG. 4: Expression of different proteins in *E. coli* using pTol system. A: Expression of fusion of TolAIII with prokaryotic proteins. Lane 1, colicin N 40-76; lane 2, Δ10 T-domain colicin N; lane 3, R-dormain colicin N. Bottom panel presents an estimation of proportion of expressed protein in bacterial cells as determined from scanned gels with the software package Tina. Values reported represent average of estimation from 5-11 colonies±SD. B: Expression of fusion of TolAIII with eukaryotic proteins. Lane 1, PDK2; lane 2, NBD1 domain; lane 3, EqtII; lane 4, $PLA_2$. Values in bottom are average of estimation from 4-8 colonies±SD. C: Expression of fusion of TolAIII with membrane proteins. Lane 1, uninduced pTolT; lane 2, induced BcrC; lane 3, induced TM1. The position where expressed BcrC and TM1 should appear on the gel is denoted by an asterisk and circle, respectively. M, molecular weight marker; C, control of bacterial cells from uninduced sample of pTolT;

FIG. 5: Purification of R-domain of colicin N. Lane 1, uninduced cells containing pTolT-Rdomain vector; lane 2, induced cells; lane 3, bacterial cytoplasmic fraction; lane 4, flowthrough of Ni-NTA chromatography; lane 5, purified fusion TolT-Rdomain proteins; lane 6, purified R domain after cleavage and ion-exchange chromatography;

FIG. 6: Depicts diagrammatically various uses of a His-tagged fusion protein. (I) A TolIIIA ("Tol") fusion partner (depicted as an oval) with a $His_6$ (H6) affinity tag (depicted as a rectangle) is attached to a non-TolAIII polypeptide (depicted as a circle). (II) To obtain purified non-TolAIII polypeptide, it may be removed from the fusion protein by endopeptidase cleavage (depicted as a lightening bolt) and purified. For interaction studies and the creation of protein arrays, the fusion protein may be immobilised in a variety of ways e.g. to a Nickel Chelate substrate via the $His_6$ tag or (III) (as shown) using an immobilised tag made from all or part of a recognised TolAIII binding protein from bacteria or phage, allowing the non-TolAIII polypeptide (or the entire fusion) to be available for interaction studies. The interaction between the non TolAIII polypeptide and a molecule that recognises it (protein, DNA, carbohydrate, lipid etc) is shown in (IV). The partner is shown as a half circle;

FIG. 7: Shows a circular plasmid map of a construct used to produce a Tol-A-III and BCL-X fusion polypeptide;

FIG. 8: Shows an SDS-PAGE of expressed TolAIII-BCLXL fusion protein. Lane 1, whole cell pellet, Lane 2, supematant after ultra centrifugation, lane 3, column wash with resuspension buffer, lane 4, wash with 50 mM imidazole, lane 5, molecular weight marker, lane 6, elution with 300 mM imidazole; and FIG. 9: Shows an SDS-PAGE of thrombin-cleaved TolAIII-BCLXL fusion protein. Lane 1, whole fusion protein, Lane 2, and 4 fusion protein after thrombin cleavage, lane 3, molecular weight marker, lane 5, flow through the column, lane 6, wash, lane 7, wash with 2M NaCl, lane 8, elution with 300 mM imidazole.

EXPERIMENTAL

In our laboratory we first prepared fusion proteins between domain III of periplasmic TolA protein (TolAIII) and T domain of colicin N. Huge amounts of fusion protein was isolated when TolAIII was at the N-terminus and T-domain at the C-terminus. On the other hand, when the colicin N domain was the N-terminal partner no expression of fusion protein was obtained.

Here we describe cloning of pTolvectors that use TolAIII as a fusion partner at the N-terminal part of expressed fusion protein. We show that levels of expression of various fusion proteins are around 20% of total bacterial proteins and we were able to purify 50-90 mg of fusions per 1 of bacterial broth. We prepared different components of colicin N by the use of this system.

In Example 1, several proteins were expressed using the system. These were different parts and domains of colicin N (TolA binding box (peptide of amino acids 40-76), deletion mutant of T-domain (Δ10) and R domain), representing prokaryotic proteins. Human phospholipase $A_2$, pore-forming protein from sea anemone equinatoxin II, nucleotide binding domain 1 (NBD1) of human cystic fibrosis transmembrane conductance regulator (CFTR) and human mitochondrial pyruvate dehydrogenase kinase 2 (PDK2) were examples of eukaryotic proteins. Transmembrane proteins were represented by BcrC, a component of bacitracin resistance system from *Bacillus licheniformnis*, and transmembrane domain 1 (TM1) of human CFTR. The expression of BCL-X, an important protein in apoptosis and cancer research, as a TolAIII fusion polypeptide is shown in Example 2.

For Example 1, in all cases except for two membrane proteins the yields of fusion protein were higher than the individual proteins. The expression of small peptides and soluble proteins was consistently good. More difficult targets cleavage sequence for endopeptidases (FIG. 2). In this way fused partners can be cloned in pTol vector via BamHI or KpnI site, leaving a tag of two (Gly-Ser, SEQ ID NO: 25) or four (Gly-Ser-Gly-Thr; SEQ ID NO: 26) amino acids, respectively, at the N-terminus (see FIG. 2).

The linker between TolAIII and fused partner is, therefore, composed of flexible part (Gly-Gly-Gly-Ser; SEQ ID NO: 18) and cleavage sequence for endopeptidases (enterokinase, factor Xa or thrombin) (FIG. 2). The oligonucleotides (all oligonucleotides from MWG Biotech) with the following sequences were used as an adaptors:

```
E(+)  (5'-GATCTGATGATGACGATAAAGGATCCGGTACCTGATGAA-3'; SEQ ID NO: 27) and

E(-)  (5'-CGCGTTCATCAGGTACCGGATCCTTTATCGTCATCATCA-3'; SEQ ID NO: 28) for enterokinase;

X(+)  (5'-GATCTATTGAAGGTCGCGGATCCGGTACCTGATGAA-3';                      SEQ ID
                                                                       NO: 29)
                                                                       and X(-)  (5'-CGCGTTCATCAGGTACCGGATCCGCGACCTTCAATA-3';                      SEQ ID
                                                                       NO: 30)
                                                                       for fac-
                                                                       tor Xa;

T(+)  (5'-GATCTCTGGTTCCGCGCGGATCCGGTACCTGATGAA-3';                      SEQ ID
                                                                       NO: 31)
                                                                       and T(-)  (5'-CGCGTTCATCAGGTACCGGATCCGCGCGGAACCAGA-3';                      SEQ ID
                                                                       NO: 32)
                                                                       for
                                                                       thrombin
                                                                       cleavage
                                                                       sites.
``` were also chosen. The membrane proteins did not express at all. The human PLA, PDK$_2$ and equinatoxin expressed well but as in the case of the individual proteins much ends up as insoluble fraction. PLA has many SS bonds and PDK has consistently resisted soluble expression in other systems. The TolAIII was not able to overcome the insoluble behaviour of these fusion partners but their recovery from inclusion bodies is still possible. In Example 2, large amounts of BCL-XL were expressed.

Materials and Methods

EXAMPLE 1

Cloning of pTol Vectors:

The original vector used in cloning was a derivative of pET3c (Novagen) termed pET8c. The pET8c vector was constructed by adding to the pET3c vector nucleotides encoding methionine followed by six histidine and two serine residues downstream of the cloning site (Politou, A. S. et al., 1994, Biochemistry 33(15): 4730-4737). The pET8c vector was used for an expression of fusion between domain III of TolA (amino acids 329-421; SEQ ID NO: 13) protein and T domain of colicin N. It is T7 based expression vector with bla gene, providing ampicillin selection. The fusion protein contains a methionine followed by six histidines and two serines at the N-terminal part. This linker enables easy purification using Ni-chelate affinity chromatography. The fusion partners were linked together via BamHI site. The C-terminal end of the fusion was cloned via MluI site. The T-domain gene was removed from the vector by restricting it with BamHI and MluI. An adaptor sequence was then ligated into the vector. It was composed in such a way that it removed the BamHI site within the flexible linker, but introduced a new BamHI site just after the Newly cloned vectors were named pTolE, pTolX, pTolT and they comprise cleavage sequences for enterokinase, factor Xa, and thrombin, respectively. Fusion partners used to test the system were cloned into the pTol vectors via BamHI and MluI sites. If the nucleic acid sequence coding for a particular protein contained internal BamHI site, a KpnI site was used instead. Nine different proteins were used to test the system (Table 1). Coding sequences were amplified by PCR. Reaction mixture contained (in 100 µl total volume): 10 µl of 10× reaction buffer supplied by the producer, 2 µl of 100 mM MgSO4, 4 µl of dNTP mix (200 µM final concentration), 100 pmol of each oligonucleotide, approximately 20 ng of target DNA and 1 Unit of Vent DNA polymerase (New England BioLabs). Target DNA was obtained either from DNA cloned into plasmids (e.g. colicin sequences were from the plasmid pCHAP4 [Pugsley, A. P., 1984, Mol. Microbiol. 1: 317-325], equinatoxin sequences were from an equinatoxin-containing plasmid described in Anderluh G. et al., 1996, Biochem. Biophys. Res. Commun. 220: 437-42, and BcrC sequences were from an BcrC-containing plasmid described in Podlesek, Z. et al., 1995, Mol. Microbiol. 16: 969-976) or via direct PCR or RT-PCR from the host organism. The resulting DNA was sequenced after cloning into pTol to ensure that it corresponded to precisely to the section of the published sequence shown in the table. Typically the following cycles were used: 10 min at 97° C.; 30 cycles, each composed of 2 min denaturation at 97° C., 1 min of annealing at 58° C., 1 min of extension at 72° C.; 7 min at 72° C. and soak at 10° C. PCR fragments were purified using commercial kits (Qiagen) and restricted by an appropriate restriction endonucleases. Restricted fragments were cloned into pre-cleaved pTol vector. The correct nucleotide sequence of the fusion protein was verified by sequencing.

TABLE 1

Proteins used to test pTol fusion expression system:

| Protein | Amino acids/ SwissProt Acc. No. | Mw[a] | Plasmid | Cloning[b] Site | Oligos for PCR[d] |
|---|---|---|---|---|---|
| Colicin N 40-76 (SEQ ID NO: 33) | 40-76/P08083 | 16038 | pTolE, T, X | BamHI | 1, 2 |
| Colicin N Δ10 T-domain (SEQ ID NO: 34) | 11-90/P08083 | 18567 | pTolT | BamHI | 3, 4 |
| Colicin N R domain (SEQ ID NO: 35) | 67-183/P08083 | 24667 | pTolT | BamHI | 5, 6 |
| Human PLA$_2$ (SEQ ID NO: 36) | 21-144/P14555 & NP_000291.1[c] | 25810 | pTolT | KpnI | 7, 8 |
| Equinatoxin II (SEQ ID NO: 37) | 36-214/P17723 | 31575 | pTolE | BamHI | 9, 10 |
| NBD1 domain of human CFTR (SEQ ID NO: 38) | 460-650/P13569 | 33134 | pTolT | BamHI | 11, 12 |
| Human PDK2 (SEQ ID NO: 39) | 18-407/Q15119 | 56193 | pTolT | KpnI | 13, 14 |
| BcrC (SEQ ID NO: 40) | 2-203/P42334 | 34775 | pTolT | BamHI | 15, 16 |
| TM1 domain of human CFTR (SEQ ID NO: 41) | 2-355/P13569 | 52590 | pTolT | BamHI | 17, 18 |

[a]Mr of fusion protein calculated from the sequence.
[b]Restriction site used for cloning at the N-terminal part of the fusion protein. In all cases C-terminal site used was MluI.
[c]RefSeq accession number.
[d]Oligonucleotides to amplify the desired proteins were of the following sequences (all 5'-3'; see Table 1):

```
                                           (SEQ ID NO: 42)
 1. TTTTTGGATCCAATTCCAATGGATGGTCATGGAG (SEQ ID NO: 43)
 2. AAGGATCCAAGCTTCAAGGTTTAGGCTTTGAATTATTGTCC (SEQ ID NO: 44)
 3. TTTTTGGATCCAATGCTTTTGGTGGAGGGAAAAATC (SEQ ID NO: 45)
 4. CTCAGCGGTGGCAGCAGCC (SEQ ID NO: 46)
 5. CGCGGATCCCATGGGACAATAATTCAAAGC (SEQ ID NO: 47)
 6. GGCGAATTCACGCGTTAAAATAATAATTTCTGGCTCAC (SEQ ID NO: 48)
 7. CCGGGGTACCAATTTGGTGAATTTCCACAGAATGATC (SEQ ID NO: 49)
 8. GGCGAATTCACGCGTTAGCAACGAGGGGTGCTCCC (SEQ ID NO: 50)
 9. CGCGGATCCGCAGACGTGGCTGGCGCC (SEQ ID NO: 51)
10. GGCGAATTCACGCGTTAAGCTTTGCTCACGTGAGTTTC (SEQ ID NO: 52)
11. CGCGGATCCTCTAATGGTGATGACAGCCTC (SEQ ID NO: 53)
12. GGCGAATTCACGCGTTAGAAAGAATCACATCCCATGAG (SEQ ID NO: 54)
13. CCGGGGTACCAAGTACATAGAGCACTTCAGCAAGTTC (SEQ ID NO: 55)
14. GGCGAATTCACGCGTTACGTGACGCGGTACGTGGTCG (SEQ ID NO: 56)
15. CGCGGATCCTTTTCAGAATTAAATATTGATG (SEQ ID NO: 57)
16. GGCGAATTCACGCGTTAAAAGTTCTTCGATTTATCG (SEQ ID NO: 58)
17. CGCGGATCCCAGAGGTCGCCTCTGG (SEQ ID NO: 59)
18. GGCGAATTCACGCGTTAGGGAAATTGCCGAGTGAC
```

Expression of Proteins in *E. coli*

All proteins were expressed in an *E. coli* BL21(DE3) pLysE strain (from Novagen). The strain was transformed with plasmid and grown on LB plates with appropriate selection (Ampicillin, Chloramphenicol). One colony was used to inoculate 5 ml of LBAC medium (Ampicillin at 100 μg/ml, Chloramphenicol at 34 μg/ml, both from SIGMA). Bacteria were grown on rotating wheel at 37° C. After 60 min the expression of recombinant proteins was induced by an addition of 1 mM (final) IPTG and bacteria were grown for additional 4 h. Small samples (corresponding to a volume of bacteria which when resuspended in 1 ml yields $A_{600}=0.5$) was analysed on SDS-PAGE. Gels were stained with Coomassie and scanned at 600 dpi using commercial scanner. The amount of expressed proteins was estimated from the gels using the program Tina 2.0. For large-scale expression, 5 ml of bacterial culture in stationary phase was used to inoculate 250 ml of LBAC medium and grown at 37° C. in orbital shaker at 180 rpm overnight. The next morning 20-25 ml of overnight culture was used to inoculate 500 ml of M9 LBAC medium. In total 3-5 l of bacterial culture were grown for a single protein. Bacteria were grown at the same conditions until $A_{600}$ reached approximately 0.8. Then the production of recombinant proteins was induced by adding IPTG to final 1 mM concentration. Bacteria were grown for additional 4-5 h, centrifuged for 5 min at 5000 rpm at 4° C., and stored at −20° C.

Isolation of Proteins from Bacteria

Pelleted bacteria were resuspended (2 ml of buffer/g of cells) in 50 mM $NaH_2PO_4$, pH 8.0, 300 mM NaCl, 10 mM imidazole, 20 mM β-mercaptoethanol (buffer A), with following enzymes and inhibitors of proteases (final concentrations): DNase (10 µg/ml), RNase (20 µg/ml), lysozyme (1 mg/ml of buffer), PMSF (0.5 nM), benzamidine (1 mM). They were incubated on ice for an hour and occasionally vigorously shaken. The resuspended bacteria were sonicated for 3 min with a Branson sonicator and then centrifuged in a Beckman ultra-centrifuge at 40000 rpm, 4° C. in 45ti rotor. Supernatant was removed and placed at 4° C. Pellet was resuspended in the same buffer without enzymes and inhibitors (1 ml/g of weight) and kept on ice for 15 min. Centrifugation at the same conditions followed after additional 1 min of sonication. Supernatants from both centrifugations were merged and applied at approximately 1 ml/min to 1-3 ml of Ni-NTA resin (Qiagen) equilibrated with buffer A. Typically, column with bound protein was washed with two fractions of 3 ml of buffer A, two fractions of buffer A with 20 mM imidazole and 6-10 fractions of buffer A with 300 mM imidazole. Fractions were analysed on SDS-PAGE. Fractions of interest were pooled and dialysed three times against water (5 l) at 4° C. Purity was checked by SDS-PAGE. Proteins were stored at 4° C. in 3 mM $NaN_3$. Protein concentration was determined by using extinction coefficients calculated from the sequence.

Fractionation of Bacterial Proteins

All bacterial proteins were fractionated in order to see the amount of insoluble expressed proteins. Pelleted bacteria from 100 ml of broth were resuspended in 40 ml of 20% sucrose, 1 mM EDTA, 30 mM Tris-HCl, pH 8.0 and incubated 10 min at room temperature. They were centrifuged at 9000 g for 10 min at 4° C. Supernatant was removed and pellet was gently resuspended in 8 ml of ice-cold 5 mM $MgSO_4$. Bacteria were gently shaken and incubated on ice for 10 min. Bacterial protoplasts were centrifuged again at the same conditions. Supernatant was removed as periplasmic fraction. Pellet was resuspended in 10 ml of 20 mM $NaH_2PO_4$, pH 8.0, with 1 mg of lysozyme and benzamidine. It was shaken vigorously and incubated on ice for 30 min, and finally, sonicated 5×30 s. Cytoplasmic proteins were removed from insoluble material by centrifugation at 35 000 g at 4° C. for 30 min. Supernatant was removed as cytoplasmic fraction and pellet was resuspended in 2 ml of 8 M urea, 10 mM Tris-HCl, pH 7.4, 0.5% Triton X-100 as insoluble fraction (membrane proteins and putative inclusion bodies).

Cleavage and Purification of TolAIII-R-Domain Colicin N Fusion

Pure R-domain of colicin N was produced using the pTol expression system. 45 mg of TolAIII-R-domain was incubated in 35 ml of cleavage mixture at 20° C. for 20 h. Cleavage mixture contains buffer as specified by producer and thrombin (Restriction grade, Novagen) at 0.1 U/mg of fused protein. Cleaved products were dialysed three times against 5 l of 40 mM Tris-HCl, pH8.4 at 4° C., each time at least 4 h. Cleaved R domain was separated from TolAIII and uncleaved fusion protein by ion-exchange chromatography on FPLC system (Pharmacia). Proteins were applied to Mono S column (Pharmacia) at 1 ml/min in 40 mM Tris-HCl, pH8.4. After unbound material was washed from the column, R-domain was eluted by applying gradient of NaCl from 0 to 500 mM in the same buffer in 30 min. Large peak at approximately 70% of NaCl (app. 350 mM) was collected and checked for purity by SDS-PAGE.

EXAMPLE 2

Cloning of pTol Vector

A DNA fragment encoding BCL-XL (SEQ ID NO: 62) was amplified by PCR from the plasmid pETBCLXL using the oligonucleotides SenseBCL-STU (5'-TTT TTT AGG CCT TCT CAG AGC AAC CGG GAG-3'; SEQ ID NO: 60) and Mlu-BCL-Rev (5'-TTT TAC GCG TTC ATT TCC GAC TGA AGA G-3'; SEQ ID NO: 61). BCL-XL (SEQ ID NO: 62) was introduced into pTOLT plasmid using StuI and MluI restriction sites. The final plasmid was named as a pTOLT-BCLXL (FIG. 7) and DNA sequencing of this plasmid showed that BCL-XL (SEQ ID NO: 62) encoding DNA fragment was correctly inserted.

Protein Purification

BCL-XL (SEQ ID NO: 62) protein was expressed in an *E. coli* BL21 DE3 (pLysE) strain. The strain was transformed with plasmid and grown on LB plates with ampicillin (200 µg/ml) and chloramphenicol (35 µg/ml) selection. 5 ml of LB medium with antibiotics was inoculated with single colony and grown overnight at 37° C. A 5 ml overnight culture was introduced into 500 ml of LB medium in 2 liter flasks containing ampicillin and chloramphenicol. Bacteria were grown until $OD_{600}$: 0.8 and induced by addition of final concentration 1 mM IPTG then grown for additional 3 hours. Cells were harvested and resuspended in 20 mM phosphate, 300 mM NaCl, pH: 8.0 buffer containing RNAse, DNAse, PMSF (1 mM) and Benzamidine (1 mM). The cells were lysed by French press and the supernatant was obtained by ultra-centrifugation at 40 000 rpm for 1 h. The N-terminal 6× Histidine-tag (SEQ ID NO: 8) facilitated purification of the Tol-BCL fusion by means of Ni-NTA affinity column. The fusion protein was washed onto the column with 20 mM phosphate, 300 mM NaCl, pH: 8.0, buffer, additionally washed with the same buffer containing 50 mM imidazole and eluted in 300 mM imidazole, pH 7.0. The expression of fusion protein was analysed by SDS-PAGE (FIG. 8) and concentration of protein was determined by UV absorption at 280 nm.

Figure 9:
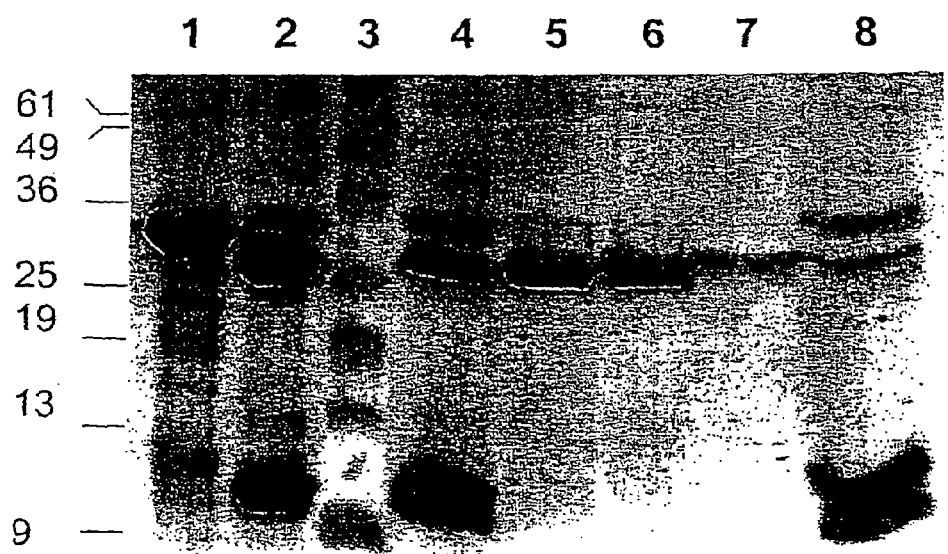

Thrombin Cleavage of the BCL-XL Protein 20 mg of TolA-BCL fusion was incubated in 20 ml of cleavage buffer at 4° C. for 4 h. Cleavage buffer contains 50 mM Tris-HCl, 150 mM NaCl, 2.5 mM $CaCl_2$, 5 mM DTT and Thrombin (1Unit of thrombin (Sigma)/mg of fused protein). The released protein was recovered applying overnight dialysed cleavage mixture to a Ni-NTA column. After unbound protein was washed from the column, remains of the BCL-XL (SEQ ID NO: 62) protein was washed by 2 M NaCl. All flow through and washes were collected and analysed by SDS-PAGE (FIG. 9). The protein yields were calculated after thrombin cleavage using UV absorbance at 280 nm.

Results

Expression of TolAIII Protein in *E. coli*

In Example 1, the third domain of TolAIII with tags (FIG. 2) was expressed from three different expression vectors (FIG. 3), pTolE, pTolT, and pTolX. In each case, the expression of TolAIII was huge, sometimes reaching up to 40% of all bacterial proteins (see FIG. 3A). Specifically, the amount of expressed TolAIII from pTolT was 26.96%±1.67

(n=5). The amount of expressed TolAIII was approximately the same regardless which vector was used. TolA expressed in bacteria did not interfere with normal bacterial metabolism. The growth curve was very similar for induced and non-induced bacteria (FIG. 3B). Ali of the TolAIII protein was expressed in soluble form. No inclusion bodies were revealed by visual inspection of pelleted remains of bacteria after osmotic lysis, lysozyme treatment, sonication, and centrifugation. Furthermore, none of the TolAIII was found in insoluble cell fraction after fractionation of proteins from bacteria. Insoluble fraction represents membrane proteins and should contain also recombinant proteins in inclusion bodies (FIG. 3C). Bacteria containing TolAIII were a bit more fragile than normal. TolAIII was released from the cells already after mild hypo-osmotic treatment, which should release only periplasmic proteins.

Expression of other Proteins in E. coli as Fusions with TolAIII

Ten proteins were tested in order to check the suitability of pTol expression system for expression and preparation of other proteins (see Example 1, Table 1, and Example 2). These were different parts and domains of colicin N (TolA binding box (peptide of amino acids 40-76), deletion mutant of T-domain ($\Delta$10) and R domain), representing prokaryotic proteins. Human phospholipase A$_2$, pore-forming protein from sea anemone equinatoxin II, nucleotide binding domain 1 (NBD1) of human cystic fibrosis transmembrane conductance regulator (CFTR), human mitochondrial pyruvate dehydrogenase kinase 2 (PDK2) and BCL-XL (SEQ ID NO: 62) were examples of eukaryotic proteins. Transmembrane proteins were represented by BcrC, a component of bacitracin resistance system from B. licheniformis, and transmembrane domain 1 (TM1) of human CFTR. Proteins chosen represent variations in size (app. 4.4 of colicin 40-76 kDa vs. 44 kDa of PDK2), genetic code (prokaryotic vs. eukaryotic proteins), protein location (soluble vs. membrane), and disulphide content (PLA$_2$, 7 disulphides vs. equinatoxin, none). Fusion proteins were expressed at high proportion in E. coli using pTol system (FIG. 4). Again, the expression was as high as 40% in some cases, but the average was around 20-25% (see FIGS. 4B and C bottom panels). The only two exceptions were membrane proteins, BcrC and TM1. In this case a band corresponding to their size was lacking from the gel (FIG. 4C). As opposed to expression of TolAIII alone, expression of fusion proteins interferes with the growth of bacteria. In the case of PLA$_2$ and membrane proteins, TM1 and BcrC, the amount of bacteria at the end of the growth halved in some cases. Interestingly, expression of fusion of PDK2 in bacterial cell had positive effect and there was always slightly more bacteria at the end of the growth (not shown). Some of the bacteria expressing fusions were further fractionated. PDK2 and PLA2 were expressed as insoluble inclusion bodies. EqtII and R-domain were found mainly in the insoluble fraction, but some proportion was found also in cytoplasmic fraction (10-25% of expressed proteins) (not shown).

Isolation and Cleavage of Fusion Proteins

In Example 1, expressed fusions were isolated from the cytoplasm by simple extraction into buffered solution, which was applied onto Ni-NTA column. By this single step proteins were already more than 95% pure (FIG. 5). Yields of isolated fusions were on average approximately 50 mg/l of bacterial broth, but reached up to 90 mg/l (Table 2). Even proteins, which were mainly expressed as inclusion bodies, were isolated in significant quantities by this procedure, i.e. 11 mg/ml of EqtII fusion was isolated. One of the fusion proteins, TolE-Tdomain 40-76, was used for the preparation of a peptide sample suitable for structure determination by NMR. It was expressed in M9 minimal media containing $^{15}N_4Cl$. Even in minimal media it was possible to express and produce fusion at significant amounts, almost 70 mg of pure fusion was obtained per litre of bacterial culture.

TABLE 2

Yields of isolated fusion proteins by using pTol system

| Protein[a] | Yield (mg/l bacterial broth) |
|---|---|
| TolE-Tdomain 40-76 | 46.7 |
| $^{15}$N TolE-Tdomain 40-76 | 67.1 |
| TolT-Tdomain 40-76 | 83.8 |
| TolX-Tdomain 40-76 | 89.6 |
| TolT-$\Delta$10 Tdomain | 37.4 |
| TolT-Rdomain | 51 |
| TolE-EqtII | 11 |
| TolT-PDK | 1.4 |

[a]Proteins are named after plasmid used for expression of fusion protein.

Pure R-domain was prepared from TolT-Rdomain fusion by cleavage with thrombin and separation of cleavage products by ion-exchange chromatography. The results of such purification scheme are presented on FIG. 5. By the outlined procedure 13 mg of pure functional R domain was prepared from 1 l of starting bacterial culture. Slightly lower yield as expected from the amount of soluble fusion is a consequence of R-domain precipitation during the preparation. However, yield presented here is still more than two times higher than the system which provides directly expressed R-domain.

We show in Example 2 that BCL-XL (SEQ ID NO: 62), an important protein in apoptosis and cancer research, can be expressed in large quantities as a fusion with TolAIII (see FIG. 8). SDS-PAGE analysis of the TolA-BCL fusion protein revealed a band with an apparent molecular weight of about 35 kD, which is in agreement with the flowing theoretical calculations:

Protparamaters of TolA-BCL fusion protein (SEQ ID NO: 14):
Number of amino acids: 348
Molecular weight: 38048.5
Theoretical pI: 5.83
Amino acid composition:

| Ala (A) | 38 | 10.9% |
|---|---|---|
| Arg (R) | 17 | 4.9% |
| Asn (N) | 17 | 4.9% |
| Asp (D) | 16 | 4.6% |
| Cys (C) | 3 | 0.9% |
| Gln (Q) | 13 | 3.7% |
| Glu (E) | 24 | 6.9% |
| Gly (G) | 29 | 8.3% |
| His (H) | 10 | 2.9% |
| Ile (I) | 12 | 3.4% |
| Leu (L) | 28 | 8.0% |
| Lys (K) | 16 | 4.6% |
| Met (M) | 7 | 2.0% |
| Phe (F) | 16 | 4.6% |
| Pro (P) | 17 | 4.9% |
| Ser (S) | 34 | 9.8% |
| Thr (T) | 13 | 3.7% |
| Trp (W) | 7 | 2.0% |
| Tyr (Y) | 10 | 2.9% |
| Val (V) | 21 | 6.0% |
| Asx (B) | 0 | 0.0% |
| Glx (Z) | 0 | 0.0% |
| Xaa (X) | 0 | 0.0% |

Total number of negatively charged residues (Asp+Glu): 40
Total number of positively charged residues (Arg+Lys): 33

Extinction Coefficients:
Conditions: 6.0 M guanidium hydrochloride, 0.02 M phosphate buffer, pH 6.5
Extinction coefficients are in units of $M^{-1} cm^{-1}$.

The first table lists values computed assuming ALL Cys residues appear as half cystines, whereas the second table assumes that NONE do.

|  | 276 nm | 278 nm | 279 nm | 280 nm | 282 nm |
|---|---|---|---|---|---|
| Ext. coefficient | 52445 | 53327 | 53190 | 52750 | 51320 |
| Abs 0.1% (=1 g/l) | 1.378 | 1.402 | 1.398 | 1.386 | 1.349 |
| Ext. coefficient | 52300 | 53200 | 53070 | 52630 | 51200 |
| Abs 0.1% (=1 g/l) | 1.375 | 1.398 | 1.395 | 1.383 | 1.346 |

The TolAIII domain was cleaved from the TolA-BCL fusion using thrombin and the BCL partner purified on a Ni-NTA column (FIG. 9). We found that 1 litre of BL21 (DE3) pLys E *E. Coli* cell culture gave 20 mg of highly pure, thrombin-cleaved BCL-XL protein. The SDS-PAGE apparent molecular weight following thrombin cleavage (see FIG. 9) was in agreement with the following theoretical calculations:

ProtParamaters of the cleaved BCLXL component TolA-BCL fusion after thrombin treatment (SEQ ID NO: 15):
Number of amino acids: 236
Molecular weight: 26329.2
Theoretical pI: 4.94
Amino acid composition:

| Ala (A) | 22 | 9.3% |
|---|---|---|
| Arg (R) | 15 | 6.4% |
| Asn (N) | 12 | 5.1% |
| Asp (D) | 10 | 4.2% |
| Cys (C) | 1 | 0.4% |
| Gln (Q) | 10 | 4.2% |
| Glu (E) | 21 | 8.9% |
| Gly (G) | 18 | 7.6% |
| His (H) | 4 | 1.7% |
| Ile (I) | 6 | 2.5% |
| Leu (L) | 19 | 8.1% |
| Lys (K) | 6 | 2.5% |
| Met (M) | 5 | 2.1% |
| Phe (F) | 13 | 5.5% |
| Pro (P) | 8 | 3.4% |
| Ser (S) | 24 | 10.2% |
| Thr (T) | 11 | 4.7% |
| Trp (W) | 7 | 3.0% |
| Tyr (Y) | 6 | 2.5% |
| Val (V) | 18 | 7.6% |
| Asx (B) | 0 | 0.0% |
| Glx (Z) | 0 | 0.0% |
| Xaa (X) | 0 | 0.0% |

Total number of negatively charged residues (Asp+Glu): 31
Total number of positively charged residues (Arg+Lys): 21

Extinction Coefficients:
Conditions: 6.0 M guanidium hydrochloride 0.02 M phosphate buffer pH 6.5
Extinction coefficients are in units of $M^{-1} cm^{-1}$.

The first table lists values computed assuming ALL Cys residues appear as half cystines, whereas the second table assumes that NONE do.

|  | 276 nm | 278 nm | 279 nm | 280 nm | 282 nm |
|---|---|---|---|---|---|
| Ext. coefficient | 46500 | 47600 | 47690 | 47510 | 46400 |
| Abs 0.1% (=1 g/l) | 1.766 | 1.808 | 1.811 | 1.804 | 1.762 |
| Ext. coefficient | 46500 | 47600 | 47690 | 47510 | 46400 |
| Abs 0.1% (=1 g/l) | 1.766 | 1.808 | 1.811 | 1.804 | 1.762 |

Discussion

TolAIII is expressed in huge quantities in soluble form in bacterial cytoplasm. Among the reasons for high expression of proteins in *E. coli* are most commonly cited appropriate codon usage, stability of mRNA transcript, size, content of disulphide bonds, and non-toxicity to the cell. TolAIII is small protein, with only one disulphide bond. It is very stable and monomeric in solution even at concentrations as high as 30 mg/ml (data from analytical ultracentrifugation and gel filtration, not shown). The small size and tendency not to aggregate are certainly important in tolerance of heterologous material in the cytoplasm of bacteria A further advantage of TolAIII gene is, that it is bacterial protein and as such it possesses only 5 codons (4.7% of 106 amino acids excluding protease cleavage site) rarely transcribed in *E. coli* genome. They are scattered along the sequence. An improvement of its expression could be achieved by engineering of the conformation of its mRNA transcript. It was shown that, for a high yield of transcribed RNA, sometimes the conformation of RNA should be such, that the ribosome binding site and start codon should be exposed and not involved in base pairing. In the case of TolAIII mRNA both are involved in building short stems and not always completely exposed (analysis of transcribed RNAs of 60-120 nucleotides (step of 10 nt) by Mfold on http://bioinfo.math.rpi.edu/~zukerm/). High expression of TolAIII protein in the T7 based vector and the high yields of pure product are comparable or even better than published and existing systems for production of fusion proteins in *E. coli*.

We have employed a domain of a periplasmic bacterial protein as a fusion partner in the overexpression of various proteins of bacterial and eukaryotic origin. Some small peptides or domains could be attached to TolAIII without significantly changing its size. The same amount of expressed protein would then be expected. In fact, the yield of fusion containing colicin N 40-76 peptide was the same as for TolAIII itself. The system is suitable for the preparation of eukaryotic proteins as well. In particular, the level of expression of EqII is much more improved over the published one. Approximately 20% of total expression of the fusion contrasted with approximately 5% in the case of direct expression. The majority of EqtII expressed from the pTol system is in the insoluble fraction, but isolation of the soluble cytoplasmic fraction still resulted in a large improvement in yield over the published method. The pTol system might also be applicable for proteins expressed as inclusion bodies. For example, the amount of expressed $PLA_2$ is similar to other expression systems, however the fusion protein can easily be isolated by Ni-NTA chromatography and then refolded and cleaved on the column matrix. An interesting observation was that the two membrane proteins studied did not express as fusion proteins with pTolA system, although the reason for this is unclear at the moment.

Three expression vectors were constructed providing three different cleavage sites for endopeptidases widely used in molecular biology, e.g. enterokinase, factor Xa and thrombin. Recognition sites for endopeptidases differ in amino acid sequence and size. These differences dramatically change properties of the small TolAIII partner in fusion proteins (Table 3). TolAT and TolAX are basic, calculated pI more than 8.5, TolAE is acid in nature, pI of 6.6. This is the result of four aspartates in the recognition sequence for enterokinase (DDDDK; SEQ ID NO: 3). The constructed vectors thus enable higher flexibility, i.e. one can easily choose appropriate vector on the basis of the properties of fused partner. In our case, R-domain of colicin N was expressed in pTolT vector since R-domain is even more basic (pI 9.7) than cleaved TolAIII. On the other hand, colicin N peptide 40-76 has almost the same pI as TolAT or TolAX. This makes subsequent purification much more difficult, the peaks representing the peptide and TolAIII would then overlap in ion-exchange chromatography. Therefore, peptide was expressed in pTolE. Cleaved TolAIII was not bound to the column at chosen conditions and the difference in pI of the uncleaved fusion (pI 7.2) and peptide was large enough to get clearly resolved peaks (not shown).

TABLE 3

Physical properties of TolAIII proteins after endoproteinase cleavage

| Protein[a] | Amino acids | Mw[b] | pI[b] |
|---|---|---|---|
| TolAE | 111 | 11716.1 | 6.57 |
| TolAT | 110 | 11593.2 | 8.93 |
| TolAX | 110 | 11583.1 | 8.57 |

[a]Proteins are named according to the vector in which they were produced.
[b]Calculated from the sequence.

We could produce functional parts of the colicin N toxin by using the pTol expression system. We produced functional R-domain and 39 residue peptide composed of colicin residues 40-76. His-tagged R-domain expresses poorly and irreproducibly and the to1A fusion expressed consistently well and improved the yield by more than two fold. Peptide was produced as $^{15}$N labelled sample for NMR structure determination. Preparation of large quantities of labelled peptide sample for NMR structure analysis can be problematic and a significant financial burden to research groups. High yields and versatility of the pTol system should make preparation of short peptides and proteins much cheaper and alternative to chemical synthesis and other expression systems. The system may be particularly useful for reproducible high level expression of small (<20 kDa) soluble proteins and unstructured peptides. For example, the system might prove useful in the preparation of $^{15}$N or $^{13}$C labelled small peptides for NMR structural studies.

The expression of BCL-XL, an important protein in apoptosis and cancer research, is difficult to express at high yield since it has a hydrophobic C-terminal region which causes instability and toxicity. Thus most structural work has been carried out on truncated versions lacking this region. We were unable to express this protein in satisfactory yields for structural studies and thus used the TolAIII fusion protein system to improve our yields. We can now express large amounts of this protein as a TolAIII fusion partner (FIG. 8). it is well folded as judged by CD spectroscopy (not shown). We can also produce large amounts in minimal media including $^{15}$NH$_4$Cl as the only nitrogen source.

The invention claimed is:

1. An isolated recombinant fusion polypeptide having an N-terminus and a C-terminus, wherein the fusion polypeptide comprises:
   (a) a fusion protein partner located towards the N-terminus of the fusion polypeptide, in which the fusion protein partner consists of a TolAIII domain defined by the amino acid sequence of SEQ ID NO: 13; and
   (b) a non-TolA polypeptide located towards the C-terminus of the fusion polypeptide, in which the non-TolA polypeptide is other than an His tag,
   wherein the fusion protein partner functions to facilitate higher levels of expression of the non-TolA polypeptide in an isolated host cell compared with expression in the isolated host cell of the non-TolA polypeptide lacking the fusion protein partner.

2. The isolated recombinant fusion polypeptide of claim 1, further comprising a signal peptide.

3. The isolated recombinant fusion polypeptide of claim 2, wherein the signal peptide is located at or near the N-terminus of the fusion polypeptide.

4. The isolated recombinant fusion polypeptide of claim 1, wherein the fusion protein partner has been codon-optimized for expression in the isolated host cell.

5. The isolated recombinant fusion polypeptide of claim 1, further comprising a linker between the fusion protein partner and the non-TolA polypeptide.

6. The isolated recombinant fusion polypeptide of claim 5, wherein the linker comprises at least one cleavage site for an endopeptidase.

7. The isolated recombinant fusion polypeptide of claim 6, wherein the cleavage site comprises one or more of the amino acid sequences consisting of the group: DDDDK (SEQ ID NO: 3), LVPR (SEQ ID NO: 4) and IEGR (SEQ ID NO: 5).

8. The isolated recombinant fusion polypeptide of claim 1, further comprising an affinity purification tag.

9. The isolated recombinant fusion polypeptide of claim 8, wherein the affinity purification tag is located at or near the N-terminus of the fusion polypeptide.

10. The isolated recombinant fusion polypeptide of claim 8, wherein the affinity purification tag is an N-terminal $His_n$ tag, with n=4, 5, 6, 7, 8, 9 or 10 (SEQ ID NOs: 6-12).

11. The isolated recombinant fusion polypeptide of claim 8, wherein affinity purification tag is an N-terminal $His_6$ tag (SEQ ID NO: 8).

12. The isolated recombinant fusion polypeptide of claim 8, in which the affinity purification tag is an N-terminal $His_n$ tag, with n=4, 5, 6, 7, 8, 9 or 10 (SEQ ID NOs: 6-12), linked to the fusion polypeptide by one or two or more Ser residues.

13. The isolated recombinant fusion polypeptide of claim 1, wherein the isolated host cell is bacterial.

14. The isolated recombinant fusion polypeptide of claim 1, wherein the isolated host cell is *Eseherichia coli*.

15. The isolated recombinant fusion polypeptide of claim 1, in which the non-TolA polypeptide is any one of the group consisting of: colicin N 40-76 (SEQ ID NO: 33), colicin N Δ10 T-domain (SEQ ID NO: 34), colicin N R domain (SEQ ID NO: 35), human $PLA_2$ (SEQ ID NO: 36), equinatoxin II (SEQ ID NO: 37), human NBD1 domain (SEQ ID NO: 38), human PDK2 (SEQ ID NO: 39), and human BCL-XL (SEQ ID NO: 62).

16. The isolated recombinant fusion polypeptide of claim 1, in which the non-TolA polpeptide excludes membrane proteins.

17. The isolated recombinant fusion polypeptide of claim 1, having the amino acid sequence defined by any one of the group consisting of SEQ ID NO: 14 and SEQ ID NO: 15.

* * * * *